US008406858B2

(12) United States Patent
Werahera et al.

(10) Patent No.: US 8,406,858 B2
(45) Date of Patent: Mar. 26, 2013

(54) MULTI-EXCITATION DIAGNOSTIC SYSTEM AND METHODS FOR CLASSIFICATION OF TISSUE

(75) Inventors: Priya N. Werahera, Aurora, CO (US); John Daily, Lafayette, CO (US); M. Scott Lucia, Larkspur, CO (US); Adrie van Bokhoven, Denver, CO (US); E. David Crawford, Denver, CO (US); Frank Barnes, Boulder, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 1223 days.

(21) Appl. No.: 11/913,042

(22) PCT Filed: May 1, 2006

(86) PCT No.: PCT/US2006/016587
§ 371 (c)(1),
(2), (4) Date: Oct. 29, 2007

(87) PCT Pub. No.: WO2006/119166
PCT Pub. Date: Nov. 9, 2006

(65) Prior Publication Data
US 2008/0194969 A1 Aug. 14, 2008

Related U.S. Application Data

(60) Provisional application No. 60/676,420, filed on Apr. 29, 2005, provisional application No. 60/718,194, filed on Sep. 15, 2005.

(51) Int. Cl.
*A61B 6/00* (2006.01)

(52) U.S. Cl. ........................................ 600/476; 600/407

(58) Field of Classification Search .................. 600/160, 600/407, 476
See application file for complete search history.

(56) References Cited

U.S. PATENT DOCUMENTS

| 4,930,516 A | 6/1990 | Alfano et al. |
| 5,042,494 A | 8/1991 | Alfano |

(Continued)

FOREIGN PATENT DOCUMENTS

| EP | 1 559 363 A2 | 8/2005 |
| WO | 9603923 A1 | 2/1996 |

(Continued)

OTHER PUBLICATIONS

International Search Report dated Apr. 3, 2007, prepared by the U.S. Patent and Trademark Office as International Searching Authority for international application PCT/US2006/016587, 2 pages.

(Continued)

*Primary Examiner* — Brian Casler
*Assistant Examiner* — Nasir S Shahrestani
(74) *Attorney, Agent, or Firm* — Senniger Powers LLP

(57) ABSTRACT

Methods and systems for in vivo classification of tissue are disclosed. The tissue is irradiated with light from multiple light sources and light scattered and fluoresced from the tissue is received. Distinct emissions of the sample are identified from the received light. An excitation emission matrix is generated (1002). On-diagonal and off diagonal components of the excitation emission matrix are identified (1004, 1006, 1008). Spectroscopic measures are derived from the excitation emission matrix (1014), and are compared to a database of known spectra (1016) permitting the tissue to be classified as benign or malignant (1018). An optical biopsy needle or an optical probe may be used to contemporaneously classify and sample tissue for pathological confirmation of diagnosis.

28 Claims, 31 Drawing Sheets

U.S. PATENT DOCUMENTS

| | | | |
|---|---|---|---|
| 5,131,398 | A | 7/1992 | Alfano |
| 5,280,788 | A | 1/1994 | James et al. |
| 5,368,045 | A | 11/1994 | Clement et al. |
| 5,983,125 | A | 11/1999 | Alfano et al. |
| 6,124,358 | A | 9/2000 | Estanove et al. |
| 6,174,291 | B1 | 1/2001 | McMahon et al. |
| 6,405,074 | B1 | 6/2002 | Banerjee |
| 6,485,413 | B1 * | 11/2002 | Boppart et al. ............... 600/160 |
| 6,564,087 | B1 * | 5/2003 | Pitris et al. .................... 600/478 |
| 2003/0055341 | A1 | 3/2003 | Banerjee |
| 2003/0135122 | A1 | 7/2003 | Bambot et al. |
| 2006/0139633 | A1 | 6/2006 | Puppels et al. |
| 2010/0198080 | A1 | 8/2010 | Liu et al. |
| 2011/0319759 | A1 | 12/2011 | Liu et al. |

FOREIGN PATENT DOCUMENTS

| | | |
|---|---|---|
| WO | 9827965 | 7/1998 |
| WO | 2004/041060 A3 | 5/2004 |
| WO | 2005/092194 A1 | 10/2005 |

OTHER PUBLICATIONS

Written Opinion of the International Searching Authority dated Apr. 3, 2007, prepared by the U.S. Patent and Trademark Office as International Searching Authority for international application PCT/US2006/016587, 5 pages.

Bigio, Irving J., and Mourant, Judith R., "Ultraviolet and visible spectroscopies for tissue diagnostics: fluorescence spectroscopy and elastic-scattering spectroscopy," Phys. Med. Biol. 42, pp. 803-814, Copyright 1997 Institute of Physics Publishing Ltd., United Kingdom.

Palmer, Gregory M., Keely, Patricia J., Breslin, Tara M., and Ramanujam, Nirmala, "Autofluorescence Spectroscopy of Normal and Malignant Human Breast Cell Lines," Photochemistry and Photobiology, 2003, pp. 462-469, Copyright 2003 American Society for Photobiology.

Palmer, Gregory M., Zhu, Changfang, Breslin, Tara M., Xu, Fushen, Gilchrsit, Kennedy W., and Ramanujam, Nirmala, Comparison of Multiexcitation Fluorescence and Diffuse Reflectance Spectroscopy for the Diagnosis of Breast Cancer (Mar. 2003), IEEE Transactions on Biomedical Engineering, vol. 50, No. 11, Nov. 2003, 10 pages.

Ramanujam, Nirmala, "Fluorescence Spectroscopy of Neoplastic and Non-Neoplastic Tissues," Review Article, Neoplasia, vol. 2, Nos. 1-2, Jan.-Apr. 2000, pp. 89-117, Copyright 2000 Nature America, Inc.

Utzinger, Urs, and Richards-Kortum, Rebecca R., "Fiber Optic Probes for Biomedical Optical Spectroscopy," Journal of Biomedical Optics, vol. 8, No. 1, Jan. 2003, pp. 121-147.

* cited by examiner

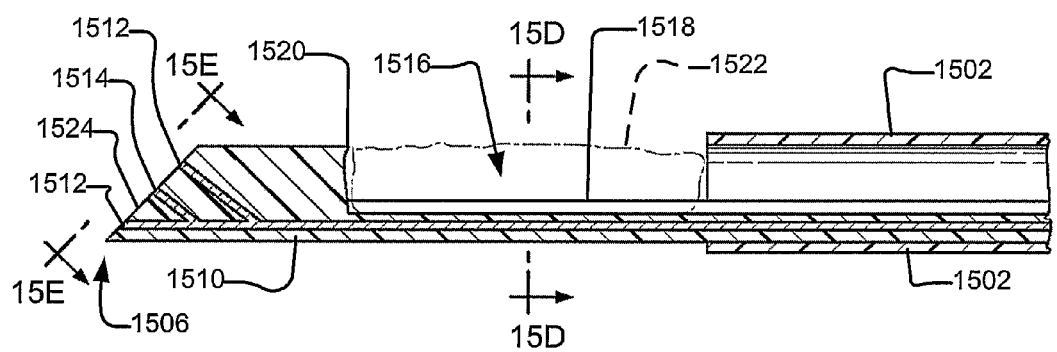
Fig. 15C
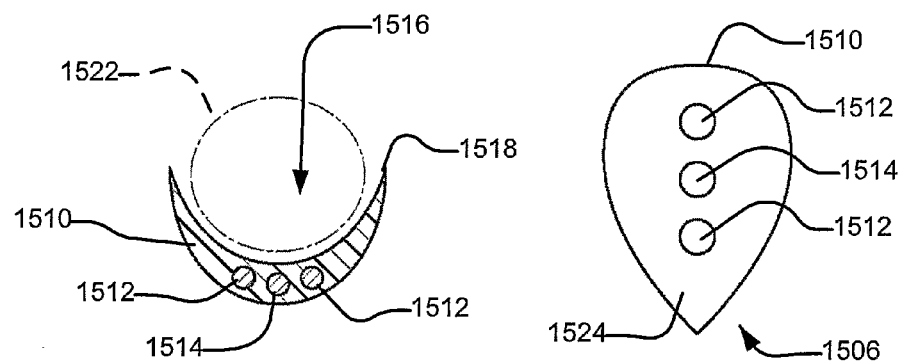
Fig. 15D     Fig. 15E

FLUORESCENCE DUE TO NADH at 340nm EXCITATION

FLUORESCENCE DUE TO NADH at 360nm EXCITATION

US 8,406,858 B2

MULTI-EXCITATION DIAGNOSTIC SYSTEM AND METHODS FOR CLASSIFICATION OF TISSUE

CROSS REFERENCE TO RELATED APPLICATIONS

This application for Letters Patent is submitted pursuant to 35 U.S.C. Section 371 and is a national stage patent application corresponding to international application no. PCT/US2006/016587, filed 1 May 2006, entitled "MULTI-EXCITATION DIAGNOSTIC SYSTEMS AND METHODS FOR CLASSIFICATION OF TISSUE," which claims the benefit of the filing date of, each of the following provisional applications, the entire disclosure of each of which is incorporated herein by reference for all purposes: U.S. provisional patent application No. 60/676,420, entitled "MULTI EXCITATION DIAGNOSTIC SYSTEMS AND METHODS," filed 29 Apr. 2005 and U.S. provisional patent application No. 60/718,194, entitled "ELECTROMAGNETIC SYSTEM FOR THE CHARACTERIZATION OF TISSUE," filed 15 Sep. 2005.

This application is also related to concurrently filed, commonly assigned, Patent Cooperation Treaty application no. PCT/US2006/017156, entitled "ELECTROMAGNETIC SYSTEM FOR THE CHARACTERIZATION OF TISSUE," the entire disclosure of which is also incorporated herein by reference for all purposes.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. NIH CA66161 awarded by the National Institutes of Health.

BACKGROUND OF THE INVENTION

This application relates generally to tissue characterization. More specifically, this application relates to methods and systems for using electromagnetic radiation to characterize tissue.

It is well known that cancer continues to be a highly destructive disease, resulting in large numbers of deaths every year. For example, approximately 30,000 new case of oral squamous cell carcinoma are diagnosed every year, resulting in an annual death rate of this type of cancer itself of about 8000. Current treatments of cancer, whether they be surgical, chemical, or radiological, have a number of complications that can greatly diminish quality of life of patients by themselves. A recognized way to avoid these complications centers around early detection of malignant cells, or of cell properties that are precursors to malignancy. Treatment options are far less invasive and damaging when these conditions are detected early.

In the case of oral cancer, for example, oral carcinoma is commonly preceded by dysplasia. Dysplastic and cancerous cells differ in their biochemical and morphological properties when compared with healthy cells, and this may, in principle, be used as a mechanism for diagnosis. Currently, such precancerous molecular or chromosomal abnormalities are largely undetectable. In addition, geographic misses frequently occur, leading to false-negative biopsies. Cancers are often multifocal—a positive biopsy at one site may not give a full picture of the extent of the disease if the cancer is multifocal or has extended to "skip areas." Furthermore, there is currently no standard technique for determining genetically abnormal tissue at resection margins in operating rooms. Such abnormalities are clinically undetectable and may lead to recurrence despite complete resection as determined by frozen section.

Prostate cancer is another example of a multifocal disease characterized by a high prevalence and marked heterogeneity of its morphology and clinical behavior. Prostate cancer remains the most common visceral cancer and the second most common cause of male cancer deaths in the United States. Nearly 1 million men are screened for prostate cancer annually in the United States. In 2006, it is estimated that 234,460 of these men will be diagnosed with prostate cancer and 27,350 will die from this disease.

Transrectal ultrasound (TRUS) guided needle biopsy is the current standard to diagnose prostate cancer. However, the clinical prostate cancer detection rate of TRUS-guided needle biopsies is only 25-30%, while more than 50% of cancers that require definitive treatment remain undetected during initial biopsies. Such undetected cancers are at high risk of spreading beyond the prostate gland and metastasizing to distant sites. Since prostate biopsies are taken randomly without any knowledge of tissue morphology, they often fail to provide an accurate pathologic/clinical stage of the disease.

Opportunities to intervene may be enhanced if accurate detection of the predisease/disease state can be achieved at the biochemical, structural, or pathological/physiological level. Presently, there are no real-time diagnostic tools available to assist the urologist in the in vivo detection of tissue abnormalities associated with prostate cancer. While TRUS images can identify prostate borders, the procedure cannot discriminate between benign and malignant prostatic tissue.

All of these factors contribute to a general need for methods and systems that permit accurate and simple in vivo characterization of tissue.

BRIEF SUMMARY OF THE INVENTION

Implementations described herein provide methods of characterizing tissue to distinguish between benign and malignant tissue. The tissue is irradiated with light and light scattered and fluoresced from the sample is received. A plurality of distinct excitations of the sample is identified from the received light. On-diagonal components of an excitation emission matrix are identified from the plurality of distinct excitations simultaneously with identifying off-diagonal components of the excitation emission matrix from the plurality of distinct excitations. The excitation emission matrix is accordingly generated from the identified on-diagonal elements and the identified off-diagonal elements. A plurality of spectroscopic measures are derived from the excitation emission matrix and fluorescence spectra, permitting the tissue to be classified according to properties of the derived plurality of spectroscopic measures.

The tissue may be classified by applying a pattern recognition technique to the derived plurality of spectroscopic measures. Derivation of the plurality of spectroscopic measures may comprise calculating a diffuse reflectance from the diagonal components of the excitation emission matrix. Certain of the spectroscopic measures may be calculated from the diffuse reflectance. Examples of spectroscopic measures that may be derived include a single scattering spectrum, a multiple scattering spectrum, and a fluorescence spectrum. In some instances, boundary-layer measurements may be removed from the plurality of spectroscopic measures.

The tissue may be illuminated with light from a plurality of different sources at different wavelengths. In one implementation, at least one of the sources is a broadband light source and another of the sources is bandwidth-limited incident light source in the UV and near UV spectrum.

In one implementation, a diagnostic software system network is trained to differentiate between benign and malignant tissue. A plurality of spectra is acquired for distinct positions of the tissue. The artificial neural network is then instructed to search for differentiating features of the spectra. Tissue specimens that correspond to the distinct positions are produce and the differentiating features of the spectra determined by the artificial neural network are compared with pathological observations of tissue specimens. Feedback is then provided to the artificial neural network based upon correlations between the pathological observations and the differentiating features.

In another implementation, morphology of tissue is determined. First, a plurality of spectra for distinct positions of the tissue is acquired. Next, the spectra are observed for distinguishing features to differentiate between benign and malignant tissue. Then each distinct position is defined as at least benign or malignant. A system for determining morphology of tissue may comprise a light source, an optical probe, a spectrometer, a detector, and a computer. A transmitting optical fiber couples the optical probe with the light source and transmits light from the light source to the optical probe. The spectrometer is coupled with the optical probe via at receiving optical fiber. The detector is coupled with the spectrometer and translates optical spectral data from the spectrometer into digital data for processing by the computer. The computer includes a processor and memory and is coupled with and controls each of the light source, the spectrometer, and the detector. An artificial neural network module stored in the memory and executed by the processor. The artificial neural network module is trained to analyze the digital data corresponding to the optical spectral data to differentiate between benign and malignant tissue.

In another implementation, tissue is spectrally classified. A cell line corresponding to a morphology of the tissue is suspended within a suspension medium. Next, a fluorometric analysis of the cell line is conducted to determine a fluorescence spectrum of the cell line. Then an excitation-emission matrix is produced corresponding to the fluorescence spectrum of the cell line.

In another implementation, an optical biopsy needle device comprises an elongate biopsy needle with a distal tip and a fiber optic bundle with at least one transmitter fiber and at least one receiver fiber. The fiber optic bundle extends within the biopsy needle and terminates at a distal end at the distal tip of the biopsy needle. The optical biopsy needle device may be used to contemporaneously classify and biopsy tissue. The optical biopsy needle device is connected with a spectral analysis device. The distal tip of the biopsy needle is positioned adjacent to or within the tissue. A spectral response associated with a distinct position of the tissue is obtained. The spectral response is evaluated with the spectral analysis device to determine whether the tissue is normal, benign, or malignant. The distinct position is then biopsied if the tissue is determined to be malignant.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components.

FIG. 15C is a side elevation view in cross section of the distal tip of the optical biopsy needle of FIG. 15A as indicated in FIG. 15B.

FIG. 15D is an end elevation view in cross section of a tissue resection feature of the optical biopsy needle of FIG. 15A as indicated in FIG. 15C.

FIG. 15E is an orthogonal view of the distal tip of the optical biopsy needle of FIG. 12A as indicated in FIG. 12C.

DETAILED DESCRIPTION OF THE INVENTION

1. Introduction

Embodiments of the invention use electromagnetic properties to characterize tissue, with specific embodiments using certain spectroscopic properties recognized by the inventors to include morphological and biochemical information that may be used to characterize tissue. Fluorescence is measured from samples and may result from intrinsic or extrinsic fluorescence. "Intrinsic fluorescence" refers to fluorescence from molecules that occur naturally in a sample while "extrinsic fluorescence" refers to fluorescence from molecules that have been added to the sample by an external mechanism.

Optical spectroscopy provides a methodology to diagnose disease by quantitatively evaluating changes in tissue morphology and composition. Light interacts with biological tissue in a variety of ways. Various types of tissue fluoresce, absorb, and scatter light in different regions of the electromagnetic (EM) spectrum and by different amounts. The optical properties of tissues are determined by their molecular composition and cellular morphology. Optical techniques utilize accurate measurements of these absorbed or scattered signals to identify benign versus malignant tissues. Based on this principle, optical biopsy techniques have been used to identify various types of surface carcinomas in real-time.

However, optical properties of different organs are very different. Optical spectroscopic features need to be established for each individual tissue type to provide identification of benign versus malignant tissue. A large majority of scattering events in biological tissue are elastic. Elastic scattering primarily probes morphological features and has proven to be sensitive to cancer grades in several locations.

Figure 1A:
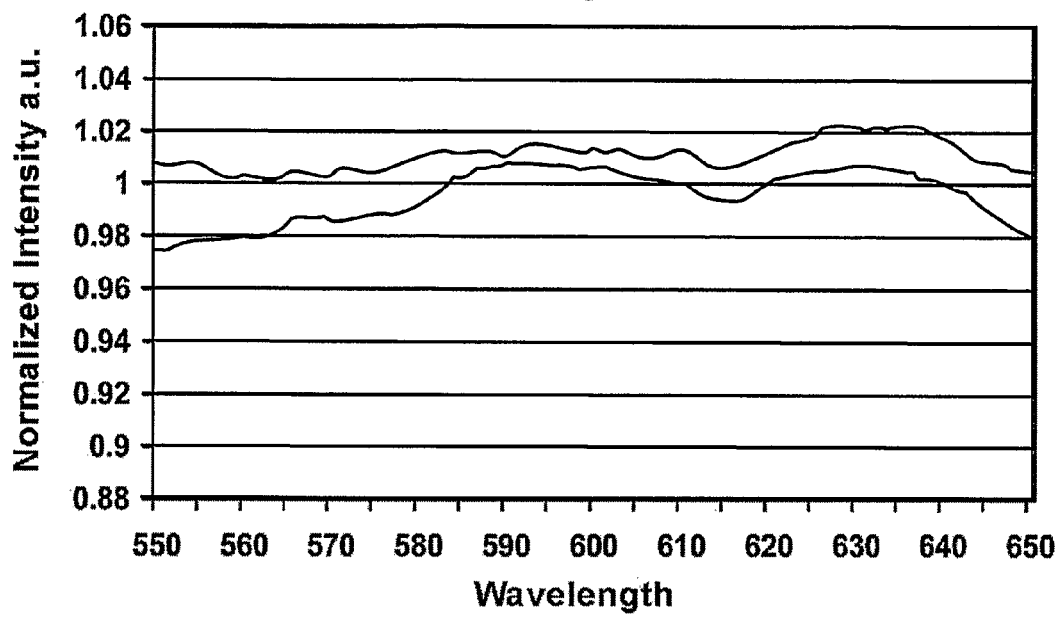
FIG. 1A is a graph depicting elastic scattering spectra for healthy prostate tissue.
Figure 1B:
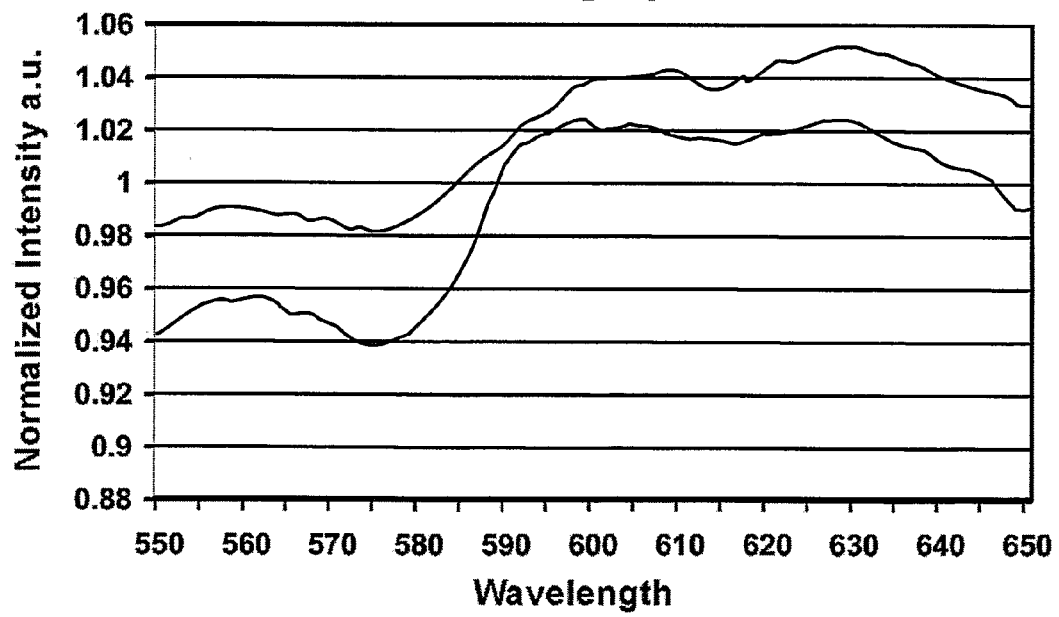
FIG. 1B is a graph depicting elastic scattering spectra for cancerous prostate tissue.

FIG. 1A illustrates the elastic scattering spectra (ESS) of normal prostate tissue. FIG. 1B illustrates the ESS of malignant prostate tissue. The upper and lower lines in each of FIGS. 1A and 1B indicate the upper and lower boundaries of a number of spectral readings obtained from surgically removed prostatectomy specimens of several patients. There is a distinct absorption feature at 580 nm, noticeably greater for malignant tissue than for normal tissue. The shape of this spectral absorption feature is consistent with the absorption spectrum of beta-carotene, a frequent constituent of lipids and cholesterol.

Another distinguishing spectral feature between FIG. 1A and FIG. 1B is the longer-scale slope variations consistent with an increase in the size distribution of the scattering centers for malignant conditions (e.g., nuclei, organelles, etc.). Some of these distinguishing spectral features are consistent with increased perfusion of malignant and pre-malignant lesions. These data indicate that determination of tissue morphology may guide prostate biopsies and direct therapeutic agents in vivo and in real-time.

Fluorescence spectra may be combined with elastic scattering spectra (ESS) to extend the classification for benign versus malignant tissue. While fluorescence is a weaker process than elastic scattering, it potentially allows for identification of specific endogenous fluorophores whose concentrations may vary with disease state. Analysis of both types of observed signals is therefore desirable. Such analysis may involve estimation of tissue scattering and fluorescence properties, solution of the scattering problem, and prediction of the effect of scattering and absorption on fluorescence signals.

Figure 2:
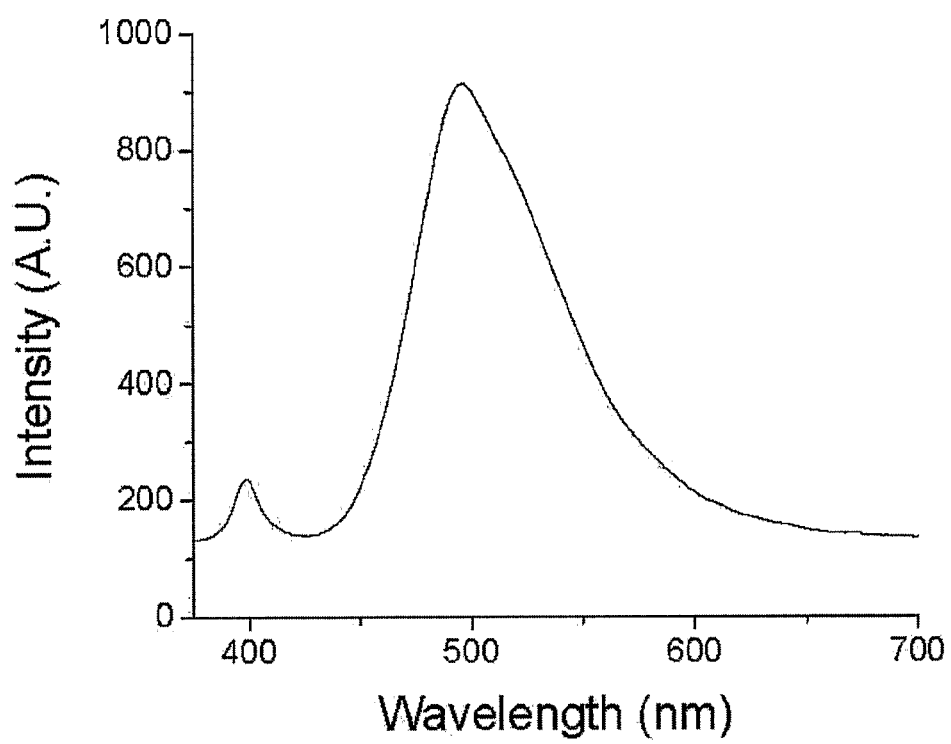
FIG. 2 provides an illustration of fluorescence spectroscopy.
Figure 27A:
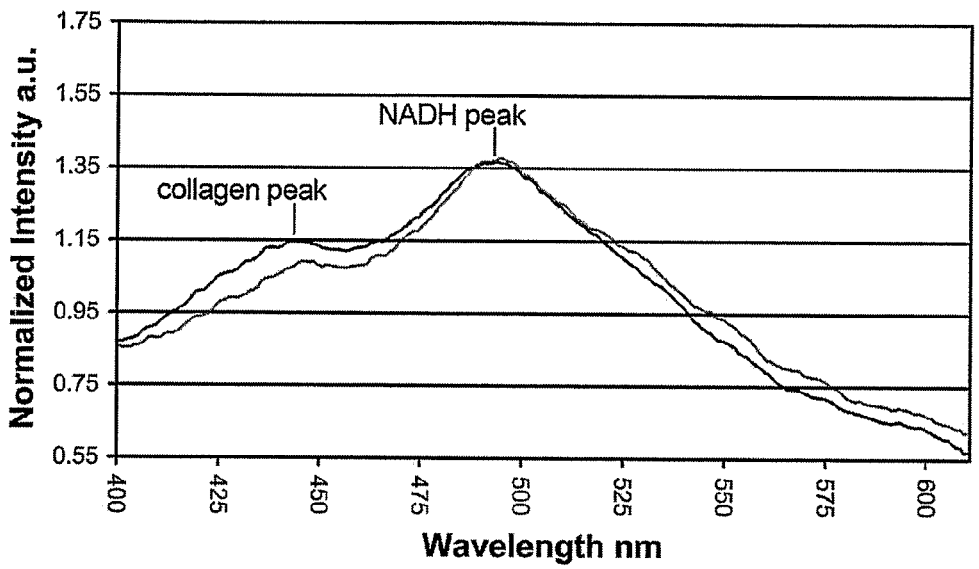
FIG. 27A is a graph depicting the fluorescence spectra of formalin-fixed, paraffin-embedded, healthy prostatic tissue.
Figure 27B:
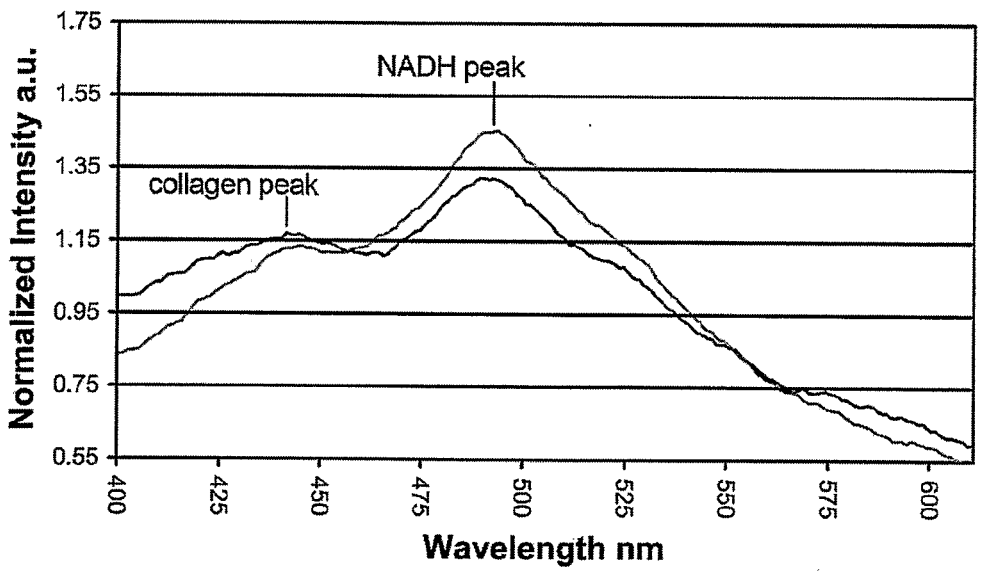
FIG. 27B is a graph depicting the fluorescence spectra of formalin-fixed, paraffin-embedded, cancerous prostatic tissue.

For purposes of illustration, FIG. 2 shows results that illustrate that fluorescence may be measured on a phantom designed to simulate oral tissue. In this instance, the phantom comprised a light-emitting-diode structure of 200 nm of a proprietary fluorescent material coated on 200 nm of polyethylenedioxythiophene ("PEDOT") coated on an InSnO-coated microscope slide. In addition, FIGS. 27A and 27B illustrate fluorescence spectra for normal and malignant prostatic tissue as described in greater detail herein.

2. Data Collection

Figure 3A:
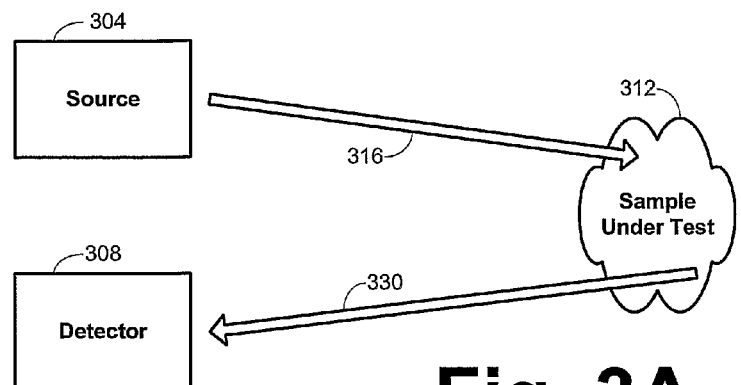
FIGS. 3A-3C are schematic illustrations of structures that may be used for electromagnetic irradiation of a sample and collection of data.
Figure 3B:
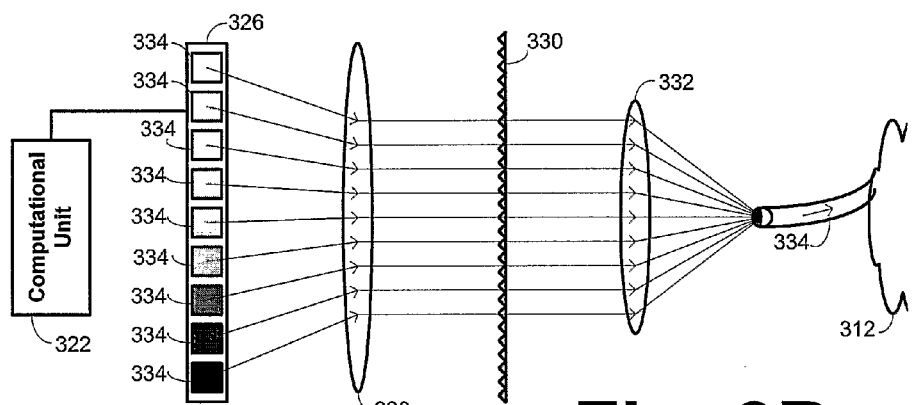
Figure 3C:
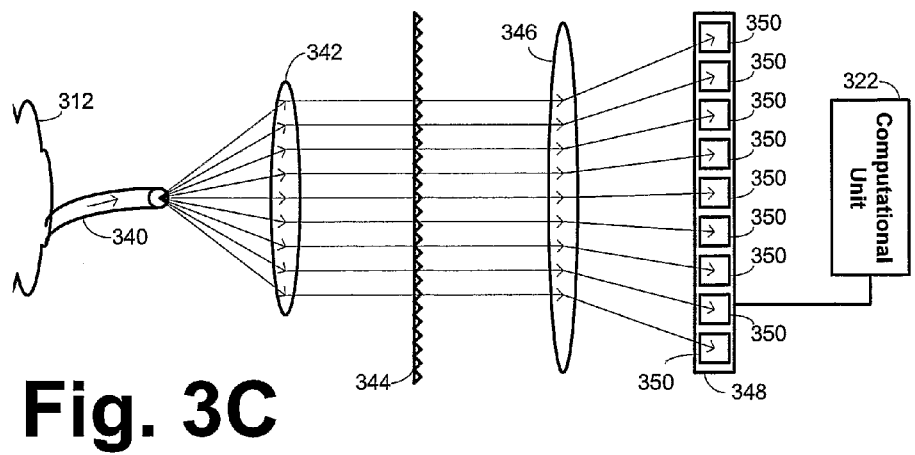

An overview of a system that may be used in embodiments of the invention to collect data for analysis is provided with FIGS. 3A-3C. FIG. 3A shows that at its broadest conceptual level, a sample under test ("SUT") 312 is evaluated by providing incident light 316 from a source 304 and receiving reflected and/or scattered light 320 from the SUT 312 at a detector 308. The source 304 may comprise multiple-excitation discrete wavelength pulsed sources spanning a portion of the spectrum, such as by spanning the visible spectrum, and/or may comprise a white-light pulsed source. The detector 308 may comprise a locked detection system.

A further illustration of the source 304 is illustrated with FIG. 3B, which shows that light may be generated by an array 326 of sources 324, which may be substantially monochromatic sources or may be broader-band sources in different embodiments. Examples of light sources 324 include inorganic light-emitting diodes, organic light-emitting diodes, laser diodes, gas lasers, solid-state lasers, fiber lasers, bulbs (halogen, tungsten, xenon, etc.), flash lamps, and the like. It is generally anticipated that different ones of the sources 324 will have different wavelengths or wavelength bands. Operation of the array 326 is controlled by a computational unit 322.

Light from the sources 324 may be collimated by a lens 328, which in some embodiments is an achromatic lens made by combining lenses of glasses having different focal powers so that the light emerging from the lens forms an image substantially free from unwanted colors. The collimated light is spectrally separated with a diffractive element 330 shown in the illustration to comprise a transmissive diffraction grating, but which may alternative comprise a reflective diffraction grating, a prism, or a grism in different embodiments.

The spectrally separated light is focused by a lens 332 onto an optical fiber 334 or other type of waveguide, which transmits the light to the SUT 312.

A further illustration of the detector 308 is illustrated with FIG. 3C, which shows that light reflected and scattered from the SUT 312 may be collected with an optical fiber 340 or other type of waveguide and subsequently collimated by a lens 342. A diffractive element 344, shown in the drawing as a transmissive diffraction grating, but alternatively comprising a reflective diffraction grating, a prism, or a grism, removes the spectral separation so that a lens 346 may direct the light to an array 348 of detectors 350. The lens 346 may advantageously again comprise an achromatic lens. Each of the detectors 350 may comprise charge-coupled devices ("CCDs") or other suitable photodetectors, with the computational unit 322 including software to analyze the spectral character of the detected light.

Figure 4:
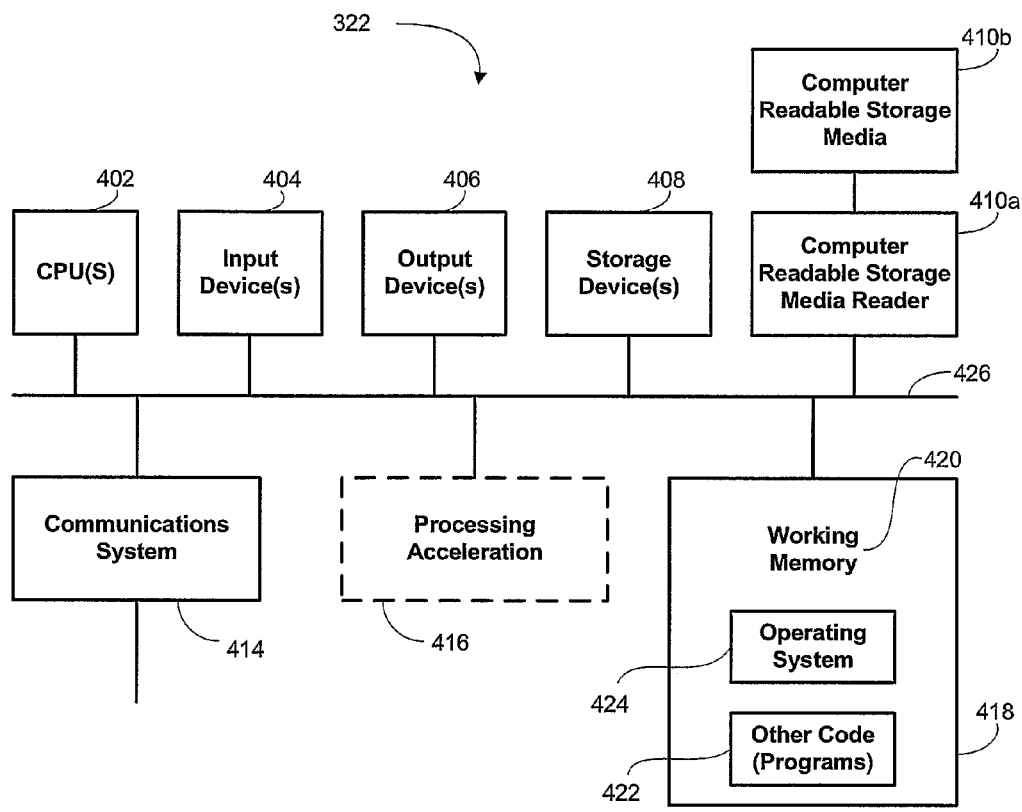
FIG. 4 is a schematic illustration of a computational system on which methods of the invention may be embodied.

A structure for the computational device 322 is illustrated schematically in FIG. 4, which broadly illustrates how individual system elements may be implemented in a separated or more integrated manner. The computational device 322 is shown comprised of hardware elements that are electrically coupled via bus 426. The hardware elements include a processor 402, an input device 404, an output device 406, a storage device 408, a computer-readable storage media reader 410a, a communications system 414, a processing acceleration unit 416 such as a DSP or special-purpose processor, and a memory 418. The computer-readable storage media reader 410a is further connected to a computer-readable storage medium 410b, the combination comprehensively representing remote, local, fixed, and/or removable storage devices plus storage media for temporarily and/or more permanently containing computer-readable information. The communications system 414 may comprise a wired, wireless, modem, and/or other type of interfacing connection and permits data to be exchanged with external devices.

The computational device 322 also comprises software elements, shown as being currently located within working memory 420, including an operating system 424 and other code 422, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

Figure 5:
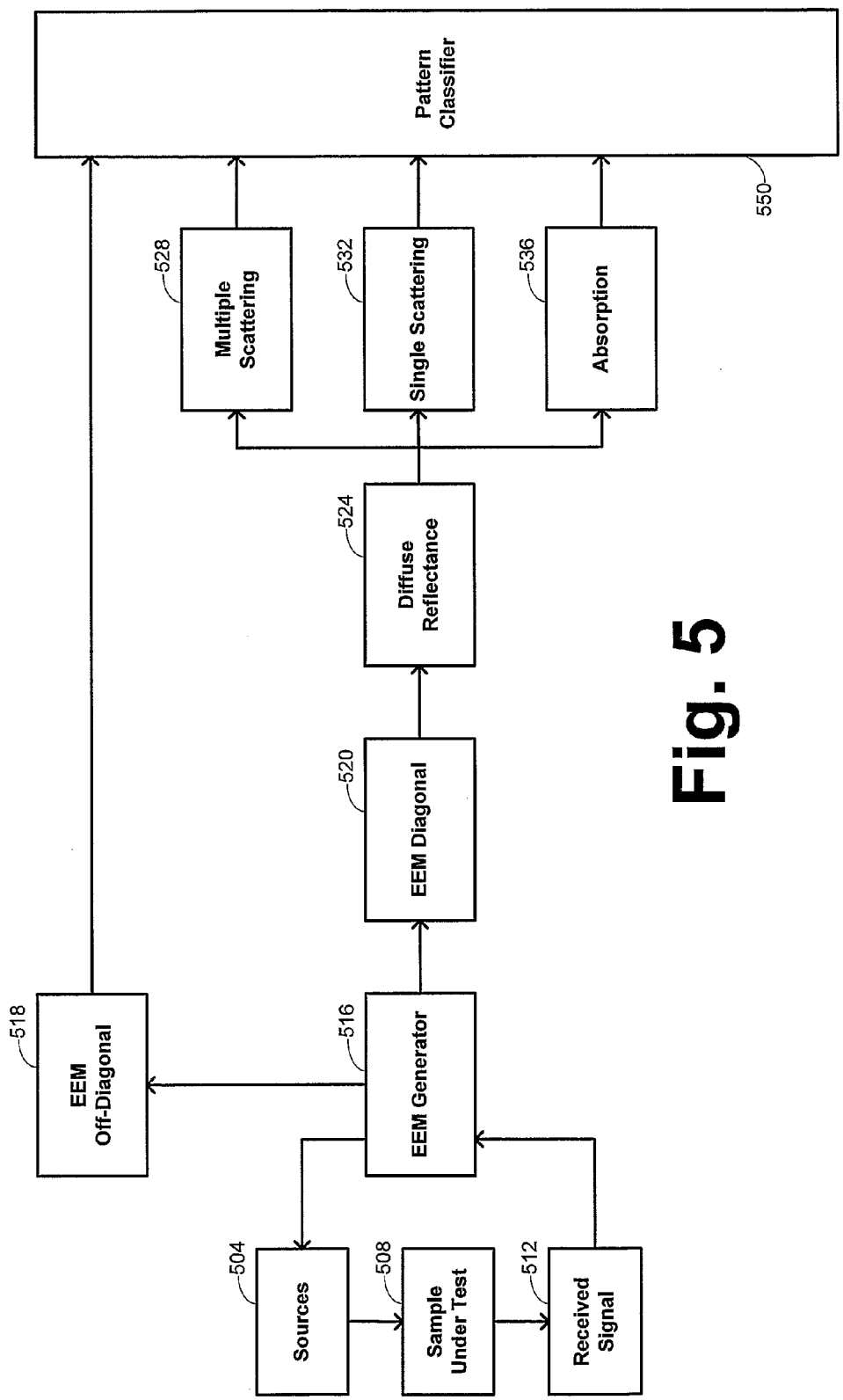
FIG. 5 is a block diagram summarizing functionality for implementing methods of the invention in some embodiments.

FIG. 5 provides a schematic overview of general system signals and data flow used in an embodiment. The light sources are designated at block 504 and may comprise a number m sources used to probe the SUT 508. Embodiments of the invention result in the generation of an excitation emission matrix ("EEM") and the broader the linewidth of the sources, the fewer the number of matrix elements that can be non-spectrally-overlapping within a given spectral region. The electromagnetic subsystem that delivers the radiation from the sources 504 to the SUT 508 may comprise a guided-wave system or a free-space system. In the case of electromagnetic waveguide delivery, the waveguide may comprise an optical fiber or other type of waveguide as illustrated in FIG. 3B. The radiation may be delivered to the SUT 508 from a waveguide that employs an aperture such that the evanescent, near-field waves of the waveguide illuminate the SUT 508 or such that the far field of the waveguide illuminates the SUT 508. The m sources may be combined spatially in a multiplexing system, free space or guided wave, or they may individually illuminate the sample at different locations through the electromagnetic subsystem.

The radiation 512 from the SUT 508 can be captured by an electromagnetic subsystem such as illustrated in FIG. 3C. The response of the SUT is first captured by this electromagnetic subsystem, which serves as the front end of an electromagnetic receiver. The purpose of the receiver is then to discriminate the collected electromagnetic radiation into n wavelength intervals of the electromagnetic spectrum. That is, the output of the receiver for a single source input is n (integrated) intensity values, each representing an integral of intensity values over some interval of the wavelength spectrum. The discrimination of the electromagnetic radiation into n integrated intensity values can be accomplished by using numerous methods, including with photodetectors having absorptive filters, spectrometers, and wavelength-selective organic photodetectors.

The correlation of responses from the SUT 508 with the individual sources 504 may be accomplished using either time-division or space-division multiplexing. In the time-division multiplexing scheme, individual sources are pulsed and the response of the SUT 508 is captured from this region only. The space-division multiplexing scheme may or may not involve the individual control of the sources in different embodiments.

Additional elements of a data collection system may include light delivery systems and collection probes. Examples of these components are further described below.

3. Data Analysis

One method of data analysis is described as follows. The matrix characterizing the SUT 404 may generated by the EEM generator 416 in the following manner. If $s_i(\lambda_s)$ is the ith intensity source spectrum (for i=1, 2, ..., m) and $r_i(\lambda_r)$ is the intensity spectral response of the tissue due to the ith source (for i=1, 2, ..., n), then the function of input wavelength $\lambda_s$ (excitation wavelength) and output wavelength $\lambda_r$ (received wavelength) that may be determined from the radiation 412 collected through the electromagnetic subsystem at the front end of the receiver is $$X(\lambda_s, \lambda_r) = s_i(\lambda_s) r_i(\lambda_r), \quad (1)$$

where the value of i takes on values from 1 to m, the number of sources. A matrix of values may be formed from this data object by having the receiver perform integrations. The total source power levels are determined from the integrals $$P_i = \int d\lambda_s s_i(\lambda_s), \quad (2)$$

where the integration interval includes all values at which the source emits power. The emission linewidth of the ith source is denoted $\Delta \lambda_{s_i}$, with the integral being performed over this linewidth. The receiver power levels are determined from integrals over intervals $\lambda_j^{\pm}$ such that the ijth component of the m×n matrix M is given by $$M_{ij} = \int_{\lambda_j^-}^{\lambda_j^+} d\lambda_r r_i(\lambda_r), \quad (3)$$

where optimal values of $\lambda_j^{\pm}$ may be determined by the experimenter and/or data processor. The source may also be parsed as the output by writing that $$S_{ij} = \int_{\lambda_j^-}^{\lambda_j^+} d\lambda_s s_i(\lambda_s). \quad (4)$$

Evidently, $$P_i = \sum_j S_{ij}. \quad (5)$$

When a spectrometer is used within the receiver, the intervals $\Delta\lambda_j = \lambda_j^+ - \lambda_j^-$ can be very fine, for example, as fine as 0.01 nm although spacings of 0.4 nm are also in use, but this example is not intended to be limiting since larger intervals may be used as well. In practice, decisions on tissue characterization may be made on some total number of features $N_f$ that is generally less than 15. In an exemplary system with eight sources, then, at most two output points per source may be of interest. But further processing may advantageously use many more points for stability and identification in the processing algorithm before the task of reducing the EEM to features is performed.

A square matrix may be generated from the n×m matrix to easily define the elastically scattered terms with the matrix diagonal. A condition on the spectral widths may be exploited to do this: When $\Delta\lambda_{s_i} \geq \Delta\lambda_j$ for all values of i and the values $n_{s_i} \approx \Delta\lambda_{s_i}/\Delta\lambda_j$ are approximated as integers, then $$n_m \approx \sum_{i=1}^{m} n_{s_i} \quad (6)$$

to define an $n_m \times n_m$ square matrix whose diagonal is nonzero but may include some off-diagonal filling. The matrix M is then considered as square with diagonal elements representing a measure of the scatting and absorption characteristics (elastic scattering elements) of the SUT 508 weighted by the spectral strength of the source in that region. Off-diagonal elements of the matrix represent a measure of higher-order nonlinear processes such as fluorescence. The diagonal is defined by the points that were generated where the $\lambda_j$ interval covers the source interval. In FIG. 5, the diagonal elements are denoted by block 520 and the off-diagonal elements are denoted by block 518.

Next, the $n_m \times n_m$ matrix may be expanded to generate an $n_c \times n_m \times n_m$ space. An algorithm is applied to the diagonal elements to separate them into $n_c$ components corresponding to various measures of scattering and absorption, while the off-diagonal elements are expanded using the identity operation. Notably, the expansion of the matrix is a completely invertible operation and none of the original information is lost.

The expansion of the diagonal elements into three components may be accomplished by first generating the diffuse reflectance vector $D(\lambda)$ from the diagonal elements of the $n_m \times n_m$ square matrix M. The diffuse reflectance is denoted in FIG. 5 by block 524 and corresponds to the elastic scattering. The vector may be generated by performing the following operation:

$$D_i(\lambda) = \sum_j \frac{M_{ij}}{S_{ij}} \delta_{ij}. \quad (7)$$

The generation of the $n_m \times n_m$ square matrix with nonzero diagonal elements results from the $S_{ij}$ used in the above equation being nonzero. In a particular embodiment, a number of operations are performed, including reduction of single scattering as indicated at block 532 and separation of the remaining diagonal elements into those that come from absorption as indicated at block 528 and those that are due to multiple scattering as indicated at block 536.

The oscillations may be split from the diffuse reflectance by subtracting the windowed average of the diffuse reflectance from the diffuse reflectance:

$$S_i = D_i(\lambda) - \sum_j W_{ij} D_j, \quad (8)$$

where $W_{ij}$ is a window function of width w. From the windowed diffuse reflectance, the remaining two elements may be extracted. This may be performed by noting the following unique features of turbid media such as tissue and absorption spectra. The diffuse reflectance due to multiple scattering contributions from particles smaller than a wavelength is a monotonically decreasing function of wavelength and for the visible region of the electromagnetic spectrum is approximately linear for scattering elements $\Delta$na<0.2 μm, where $\Delta$n is taken to be the difference in the index of refraction between the nucleus and the cytoplasm in a cell, which is approximately 0.1. The second element aiding in the separation is the broadening of absorption features for elements in tissue, which generates an imbalance in the first derivative (divided difference) of the smoothed diffuse reflectance that can be averaged out of the first derivative (divided difference) if the entire absorption feature is captured or can be balanced out of the response using centroids to balance the first derivative. The monotonically decreasing function may then be extracted from the balanced first derivative (divided difference) and subtracted from the smooth diffuse reflectance, yielding the absorption contribution of the tissue response. The monotonically decreasing function and the absorption contribution are the second and third elements of the diagonal expansion.

The new $3 \times n_m \times n_m$ space generated by the expansion of the matrix characterizing the tissue may be reduced to a number of features that are independent to enable classification of the signature from this array of digitally filtered input data. There are numerous automated techniques known to those of skill in the art for estimating the number of terms that could be used for attempting to recognize a data pattern. When too many factors are used, the recognition becomes non-unique; when too few are used, the recognition cannot be made. In embodiments of the invention, the spectral broadening in the tissue may place a limit on the minimum meaningful spectral width of a feature to be used. The inventors have found in certain investigations that this minimum is generally on the order of 30-50 nm, but identification of this value is not intended to be limiting. The diagonal of the square matrix may then be reduced to factors by summing over diagonal elements, whereas as a whole off-diagonal elements can be used in a similar manner.

A common term for methods that find the number of independent features from each data sample is "principal component analysis." When many tissue samples are lumped together such that there are $N_{samples} \times n_c \times n \times m$ arrays processed simultaneously, the techniques are often called "multispace techniques." Here, single-data-point techniques are those that are used. Once the data have been reduced to $N_f$ independent values such that the problems may be considered to be an identification problem in an $N_f$-dimensional space, permitting any of several pattern-classification techniques known to those of skill in the art to be implemented by the pattern classifier 440 to classify the result into one of $N_{patterns}$. The pattern-classification techniques may be used generally to separate the $N_f$-dimensional space by ($N_f$–1)-dimensional hyperplanes and find in which box the data point resides.

Figure 6:
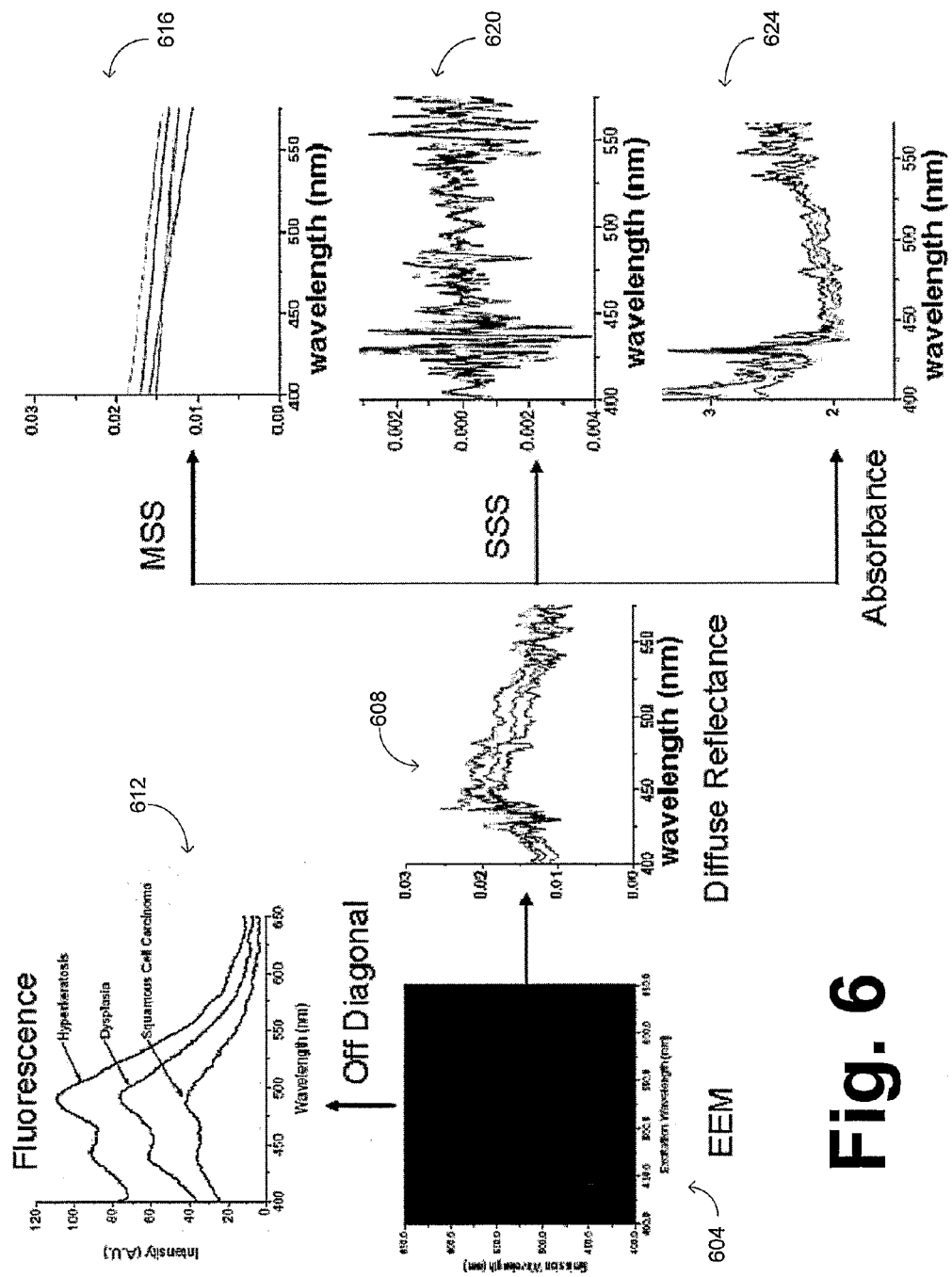
FIG. 6 provides an example of the application of the functionality of FIG. 4 to different oral-tissue samples.

An illustration of the approach described above to squamous cell carcinoma is illustrated in FIG. 6. The structure of FIG. 6 generally parallels the structure of FIG. 5, with the results for the EEM of block 516 being denoted 604, the off-diagonal elements of block 518 being denoted 612, the diffuse reflectance of block 524 being denoted 608, the single scattering of block 532 being denoted 620, the multiple scattering of block 528 being denoted 616, and the absorption of block 536 being denoted 624.

Figure 7:
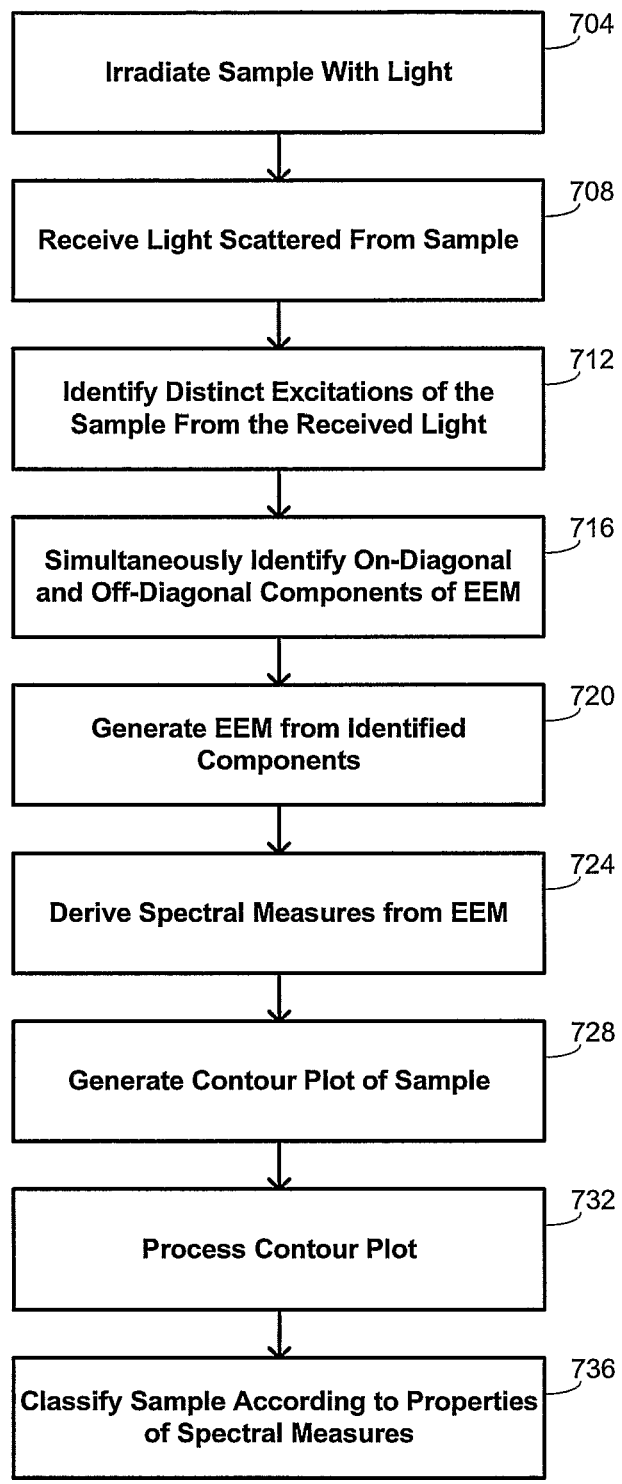
FIG. 7 is a flow diagram summarizing methods for characterizing a sample in accordance with embodiments of the invention.

The methods described above are summarized with a flow diagram in FIG. 7 that identifies specific steps that may be performed in implementations of methods of the invention. Data from a sample are collected by irradiating the sample with light at block 704 and receiving light scattered from the sample at block 708. Multiple distinct excitations of the sample are identified from the received light at block 712, which permits on-diagonal components of the EEM and off-diagonal components of the EEM to be identified simultaneously at block 716 using the techniques described above. The EEM is generated at block 720 from the identified components.

Once the EEM has been generated, it may be used at block 724 to derive a plurality of spectral measures, which in one embodiment include absorption, fluorescence, multiple scattering, and single scattering. The group of measures is used for each point within a spatial distribution to generate a contour plot of the sample at block 728. For example, in embodiments where the sample is tissue disposed on a slide, the contour plot may correspond to the spatial distribution of the slide. The contour plot may subsequently be processed at block 732. Such processing may remove extraneous information, such as by removing glass and boundary-layer measurements from tissue measurements when the sample has been prepared on a glass slide. Such removal may be accomplished with a cluster-analysis program in one embodiment, or with a generic filter that examines the fluorescence and scattering to remove data points identified as corresponding to boundary points or glass points in another embodiment.

As indicated at block 736, the spectral measures may then be used to classify the sample. In one embodiment where the sample comprises biological tissue, this is performed with a cluster analysis that separates the tissue into three categories—"normal," "dysplastic," and "cancerous." Such cluster analysis may group together items using a statistical analysis of a Euclidean distance measure in three-space generated with the fluorescence, scattering, and absorption measures.

Other methods of data analysis may include principal component, artificial neural networks (ANN), and various statistical analyses that may be employed to develop a preliminary classification scheme for in vivo diagnosis of tissue. For example, classification of ESS may be performed in a binary classification scheme using an ANN. Other alternatives include the use of logistic regression, Gaussian processes, and support vector machine algorithms to improve the classification scheme.

4. Diagnostic Devices

In one implementation, an optical probe device and techniques for diagnosis may be utilized on patients suspected of having prostate carcinoma due to an elevated serum prostate-specific antigen (PSA) and/or abnormal digital rectal exam (DRE). Instead of randomly investigating a patient's prostate by taking multiple biopsy samples, an optical probe mounted at the tip of the biopsy needle (i.e., an optical biopsy needle) may be used to explore the morphology of the prostate before extracting a tissue sample. By first conducting optical measurements, areas of carcinoma, dysplasia, or other cellular abnormalities can first be discovered to inform the locations for taking a tissue sample. A combination of ESS and fluorescence measurements may be used to determine tissue scattering properties and measure relative concentrations of fluorophores in the tissue. These optical measurements may then be compared with standard histology on the tissue sample taken to predictively determine disease state.

Figure 8:
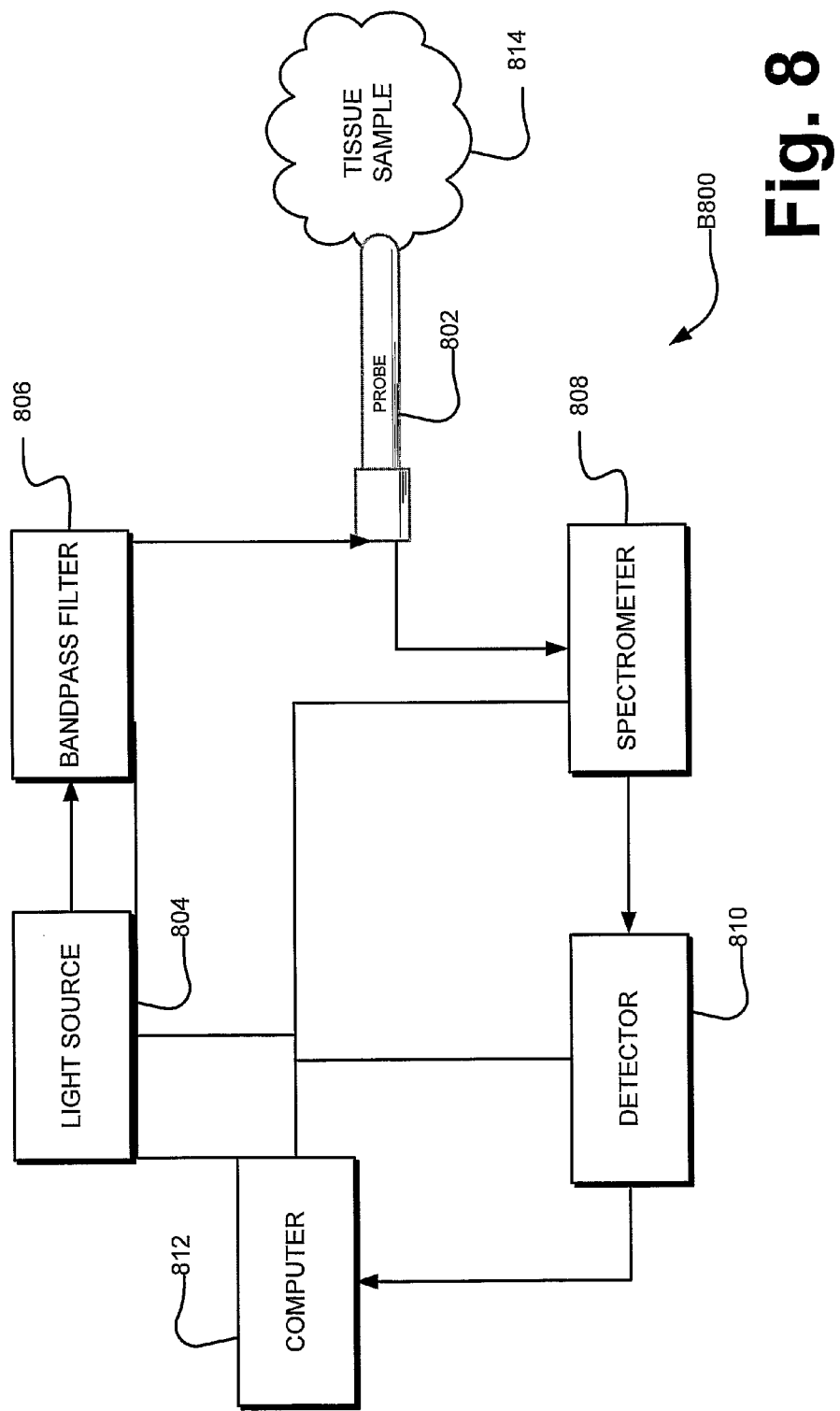
FIG. 8 is a schematic diagram of one implementation of a system for spectral analysis of tissue.

FIG. 8 depicts an exemplary system 800 for performing in vivo or ex vivo optical diagnostics of prostate tissue. The system 800 may include an optical probe 802 (for example, a stand-alone device or an optical probe mounted within a biopsy needle or a cryoprobe), which contacts the prostatic tissue 814, a light source 804, a bandpass filter 806, a spectrometer 808, a detector 810, and a computer 812. The light source 804, the bandpass filter 806, the optical probe 802, the spectrometer 808, and the detector 810 may each be connected in turn via fiber optic cabling. The computer may control each of the light source 804, the bandpass filter 806, the spectrometer 808, and the detector 810.

For elastic scattering, the light source 804 may be an Ocean Optics LS-1 Tungsten/Halogen light source and the spectrometer 808 may be an S2000 double spectrometer. The detector is generally a charge coupled device (CCD) array, which may be integral with or separate from the spectrometer 808. While a Tungsten/Halogen source offers the ability to generate an EEM that can yield information concerning scattering and absorption, such broadband sources hide fluorescent signals and cannot be modulated at a sufficient rate to yield any information that will aid in the determination of the absorption coefficient.

For fluorescence, a variety of available light sources 804 may be used including, for example, a Varian mercury arc lamp and several LED sources. In some implementations the light source 804 may provide a pulsed light output. A Jarrell Ash ¼ m monochromator may be coupled with the light sources 804 as the bandpass filter 806 for wavelength selection. Detection may be accomplished using a Princeton Instruments intensified CCD array detector as the detector 810 coupled with an Acton 300i ⅓ m Imaging Spectrometer as the spectrometer 808.

The light source 804 generates steady or pulsed light that is filtered into discrete bandwidths by the bandpass filter 806 before being output to the optical probe 802. The optical probe 802 is used to make elastic scattering and fluorescence excitation-emission measurements at different locations on the prostate. The elastic scattering and fluorescence spectra received at the optical probe 802 are transmitted to the spectrometer 808 and then passed to the detector 810. The data output from the detector 810 is transmitted to the computer.

Once the data is stored, it is arranged in a database that is processed using an ANN program or other appropriate analytical software.

One programming language that may be utilized for data collection, data processing, and for mathematical programming is Mathematica (Wolfram Research). Morphological data of prostate pathology extracted from the optical probe may include characterization of tissue as benign versus malignant and characterization of aggressiveness of the malignancy according to the Gleason sum or as low/medium/high grade.

The computer may execute Diagnostic Spectroscopy Software (DSS) to analyze the optical data returned by the probe 802, spectrometer 812, and detector 814. DSS utilizes photon migration theory for classification of biological tissue. Multiple sources with limited wavelength range and different center wavelengths are used by the DSS to determine a spectral response of tissue over a broad continuous wavelength range. Resulting spectra from multiple excitation sources may be separated into different types of light-tissue interaction mechanisms.

The DSS does not rely on single feature identifications because a single marker of a condition may not always evolve with the condition in exactly the same sequence or in exactly the same manner. Instead, the DSS monitors a number of different spectral features and their collective evolution simultaneously to increase the probability of an accurate diagnosis. The DSS may utilize any set of excitations that cover the wavelength range of interest and a DSS spectral decomposition does not require detailed tissue models. Therefore, the DSS may be used to generate an EEM, for example, as described herein above and in the examples below. Based only on the data taken, EEMs may be decomposed into auto-fluorescence spectra (AFS), tissue absorption spectra (TAS), ESS, and cell distribution spectra (CDS). These spectra can be used in conjunction with an ANN, logistic regression, or similar methods to develop an overall DSS classification scheme. The decomposed spectra may be used, for example, to train the ANN for the diagnosis of prostatic cancers and the model may be inverted for use as a diagnostic tool.

Information about a given sample in a DSS classification is not only spread across the spectrum, but also into separate and distinct spectra that are mathematically independent due to different causative events. Cancer detection requires comparison of samples of healthy tissue with pre-malignant and malignant samples. Thus, the relative changes are more important than absolute values, as they may vary strongly from subject to subject.

Figure 9:
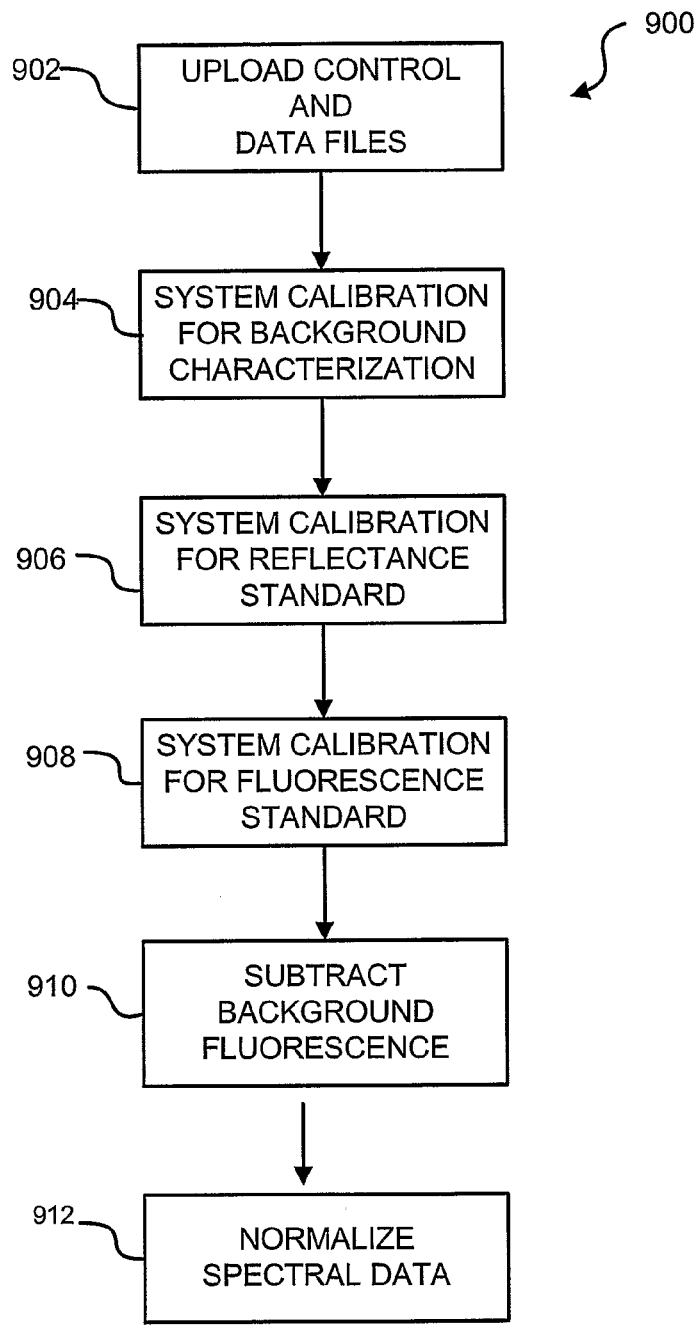
FIG. 9 is a flow diagram of an exemplary calibration method for an optical diagnostic system for tissue classification.

FIG. 9 illustrates an exemplary calibration method for a diagnostic system including an optical probe and DSS. A fiber optic probe (as described above in FIGS. 8 and 9 and in greater detail below with respect to FIGS. 14A-15E) and the DSS are calibrated for background fluorescence, reflectance and as well as for throughput prior to EEM data generation. The process of calibration begins with operation 902 wherein any control and data files in the system (e.g., in the spectrometer 808 or other components in FIG. 8 or the excitation unit 904 of FIG. 12 as described below) that are used to diagnose prostatic tissue being uploaded in the computer implementing the DSS are calibrated. In operation 204 the system is calibrated for background characterization. The probe (e.g., mounted inside the tip of a biopsy needle as described below with respect to FIGS. 15A-15E) is inserted into the prostate and spectroscopic tests identical to EEM data generation are carried out with all light sources turned-off. This enables background subtraction from tissue spectral data while the measured background is insignificant. This subtraction is performed to ensure thoroughness and consistency.

Next, in operation 906, the system is calibrated with a reflectance standard, for example, by using a white light standard such as Spectralon. In operation 908, the system is calibrated with a fluorescence standard (e.g., using Rhodamine B). Next, in operation 910 the background fluorescence is removed, e.g., by subtracting any background fluorescence. In operation 912, collected spectral data are normalized to a known peak fluorescence at a specific wavelength (e.g., Rhodamine B peak fluorescence intensity at 575 nm) to correct for variations in throughput of the probe and other components of the system.

Figure 10:
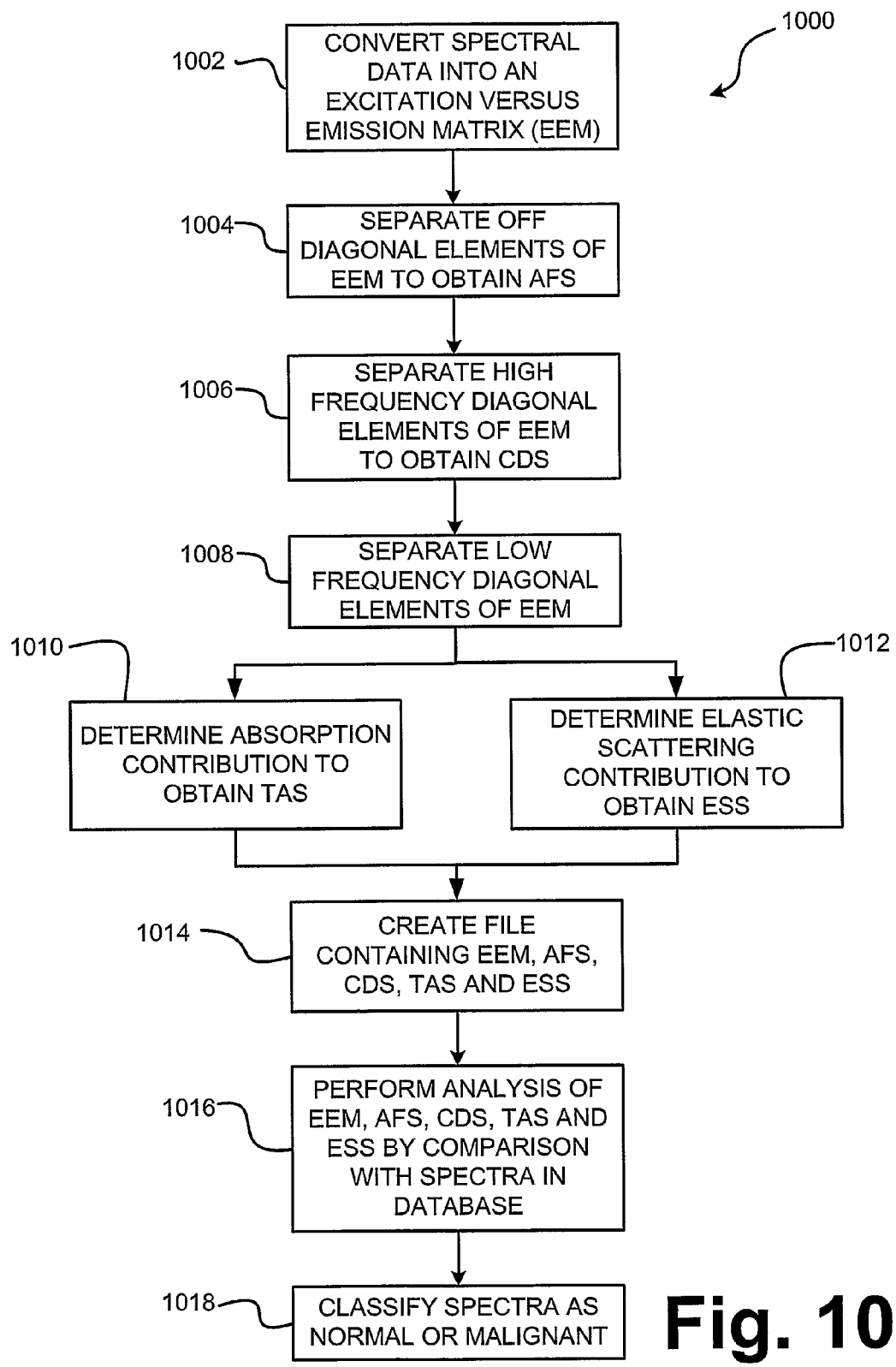
FIG. 10 is a flow diagram of an exemplary spectral data decomposition method in an optical diagnostic system for tissue classification.

FIG. 10 illustrates details of an exemplary implementation 1000 of DSS spectral data decomposition. To limit the time that is required to collect and analyze spectral data in clinical settings, the DSS decomposes spectral data using a set of rules. According to the exemplary methodology of FIG. 10, spectral data is first converted by the DSS in operation 1002 to an EEM and then decomposed in operation 1004 by separating off-diagonal from diagonal components, rapidly-varying from slowly-varying components, and absorption from scattering. In one example, the spectral components AFS, TAS, ESS, and CDS described above are separated by the identification of intrinsic versus extrinsic components. The EEM obtained in operation 1002 is thus diagonal within the spectral width of the source. The off-diagonal elements existing outside of the spectral width of the source in the EEM illustrate fluorescence from the sample for a given excitation. The AFS obtained in operation 1004 is the non-diagonal portion of the EEM.

The diagonal elements are then separated from the EEM. In operation 1006, the CDS, which is the high frequency component of the diagonal of the EEM, is separated. The low frequency component of the diagonal is then separated, in operation 1008, and is used to determine both the TAS, by determining the absorption contribution to the low frequency diagonal elements in operation 1010, and the ESS, by determining the elastic scattering contribution to the low frequency diagonal elements in operation 1012. There are numerous ways in which to effect this separation. The components of the diagonal EEM elements, absorption coefficient, the non-diagonal elements, and other information are then collected into a file in operation 1014. The data of this file is analyzed in operation 1016 by comparison to a database of spectra and classified as normal or malignant in operation 1018. Various modifications, particularly in the order of operations, may be made to operations presented in FIG. 10.

Figure 11:
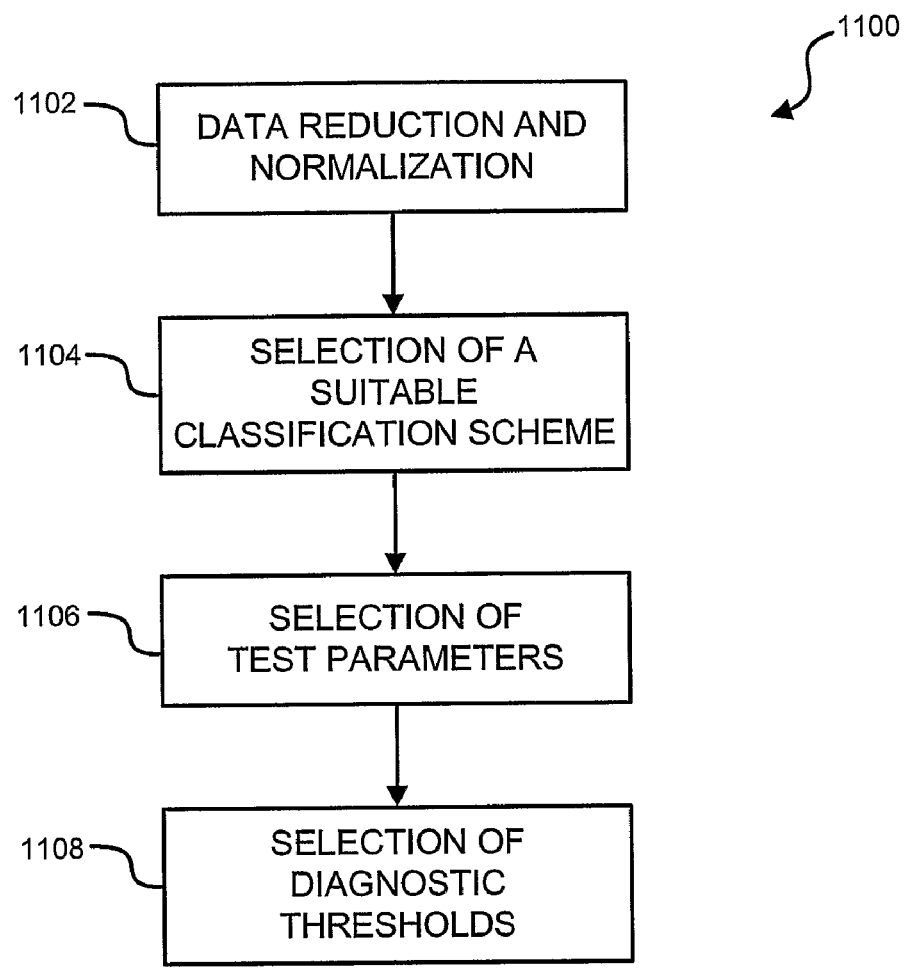
FIG. 11 is a flow diagram of an exemplary artificial neural network classification scheme for spectra data collected from tissue in an optical diagnostic system.

FIG. 11 illustrates an implementation of an exemplary ANN classification scheme 1100 for spectra collected from tissue in an optical diagnostic system. The process of ANN classification begins with data reduction and normalization in operation 1102. Spectral data in the relational database is reduced and normalized. For example, the lowest amplitude observed in the entire population may be subtracted from each data point. Normalized amplitude values may be obtained by dividing the amplitudes by the mean amplitude calculated across each specific case. The final data set may be composed of mean amplitudes over a preset wavelength range, thus condensing the data points into a more manageable representation.

Next, in operation 1104, a suitable classification scheme may be selected. For example, a simple binary classification scheme may be employed to classify benign versus malignant prostatic tissue. A two-dimensional array of data may be used in a standard three-layer, back-propagation network. Logistic regression, Gaussian processes, and support vector machine algorithms may also be used to improve the classification scheme.

The ANN classification scheme 1100 may next select test parameters in operation 1106. For example, a cancerous tissue classification scheme may be used to predict a minimum of two possible outcomes (benign versus malignant), and may incorporate parameters for cancer grade, tumor size, or tumor density in the model.

In operation 1108, the ANN classification scheme 1100 may select diagnostic thresholds. Exemplary diagnostic thresholds may be sets of values of the diagnostic parameters for AFS, TAS, ESS, CDS, and overall DSS classifications that determine the diagnostic outcome, e.g., no cancer, cancer, or cancer grade. A set of values for diagnostic thresholds may be determined based on the ability to properly predict the outcome compared to standard medical diagnostic measures. These diagnostic thresholds are dependent upon sensitivity, specificity, positive predictive value, negative predictive value, and test efficiency for the diagnostic parameters.

Figure 12:
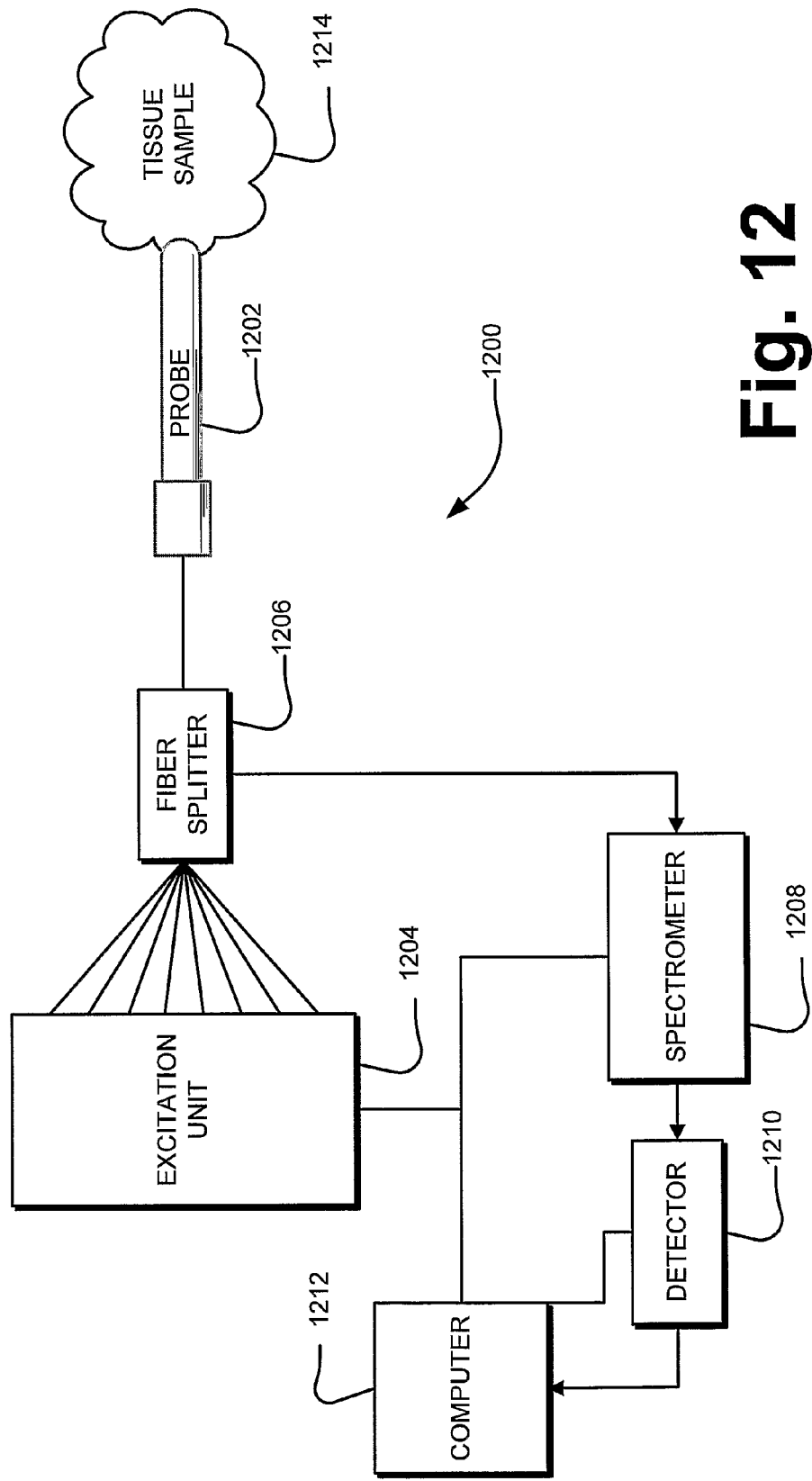
FIG. 12 is a schematic diagram of another implementation of a system for spectral analysis of tissue.

FIG. 12 depicts an alternate embodiment of a system 1200 for optical detection of tissue pathology, wherein an excitation unit 1204 takes the place of the light source 804 and bandpass filter 806 of FIG. 8. The system 1200 includes, as before, an optical probe 1202, which contacts the prostatic tissue 1214, a spectrometer 1208, a detector 1210, and a computer 1212. The system may also include a fiber splitter 1206 that collects the discrete output from the excitation unit 1204 and directs the output to one or more transmitter fibers in the optical probe 1202 as further described below. The excitation unit 904, the fiber splitter 1206, the optical probe 1202, the spectrometer 908, and the detector 910 may each be connected in turn via fiber optic cabling. The computer may control each of the excitation unit 1204, the spectrometer 1208, and the detector 1210.

Figure 13:
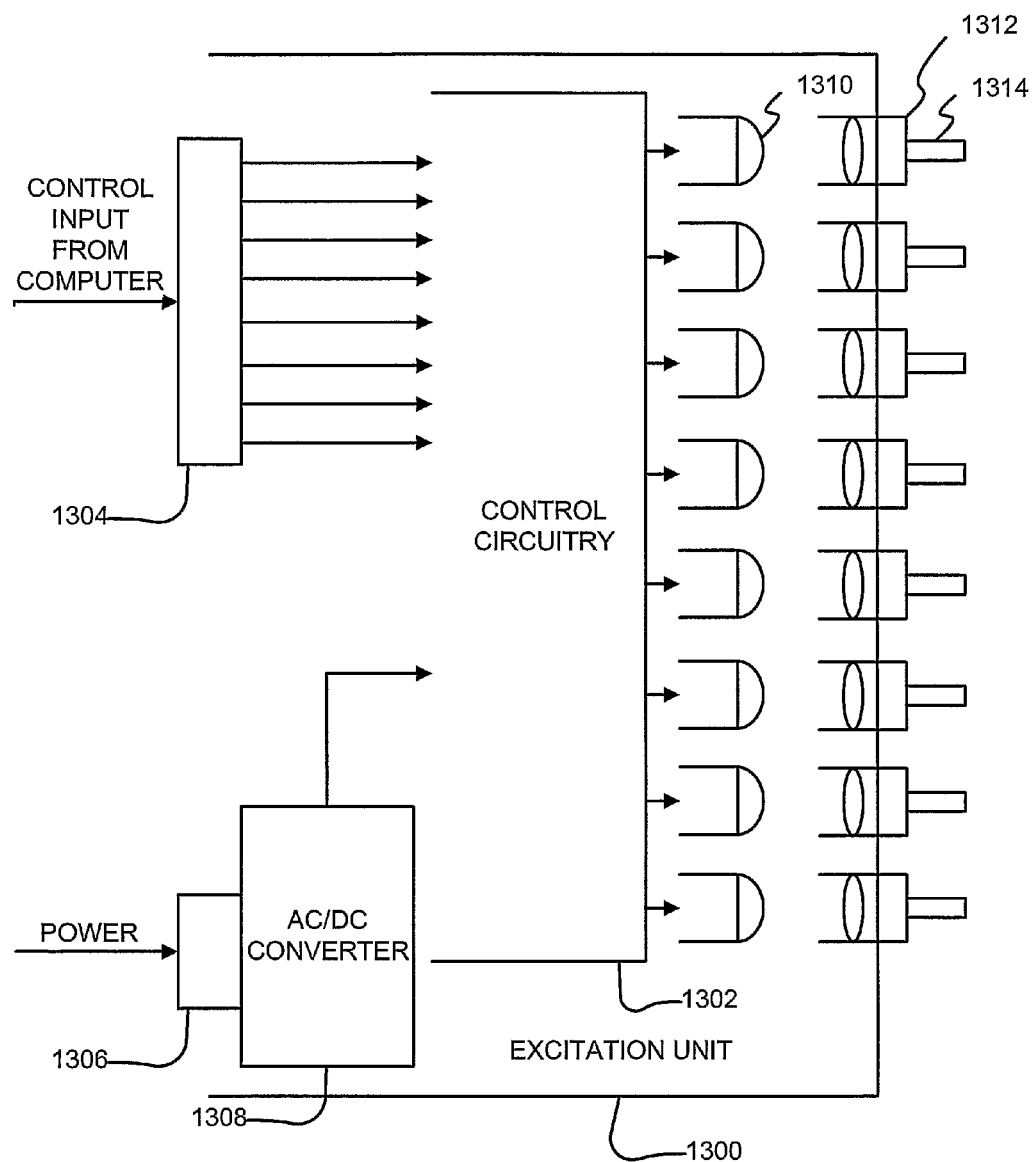
FIG. 13 is a schematic diagram of an embodiment of an excitation unit as depicted in FIG. 12.

FIG. 13 depicts an exemplary embodiment of the excitation unit of FIG. 12. The excitation unit 1300 consists of an array of surface mount light emitting diodes (LEDs) 1310 capable of excitation at different wavelengths. The LEDs in the excitation unit may individually controlled by the computer through an input port 1304 that directs control circuitry 1302 within the excitation unit 1300. The excitation unit 1000 and the control circuitry 1302 therein may be powered via a power input 1306 coupled with an AC/DC converter 1308. The LEDs 1310 may be coupled with optical fibers 1314 via focusing lenses 1312 for output of light to the optical probe. An exemplary optical fiber may be a Super Eska SH4002 multimode plastic fiber, which has a 1.0 mm core diameter made of polymethyl-methacrylate (PMMA) with a 1.0 mm cladding made of a fluorinated polymer. The numerical aperture (NA) of the fiber is 0.5 and the loss of the fiber is 190 dB/KM. The fiber is protected by a black polyethylene jacket giving the fiber a total of 4.0 mm diameter.

The emission spectrum of the LEDs 1310 in the excitation unit 1300 may have wavelengths ranging from approximately 450-650 nm. The axial intensity of the LEDs 1310 may be, for example, 160 mcd, which is approximately 3 mW at 550 nm into $4\pi$ steradians with a forward current of 20 ma. Other excitation units may, for example, employ LEDs with axial intensities of 1600 mcd as well as modulation circuitry to aid in the determination of the absorption coefficient of the tissue. The LEDs 1310 in the excitation unit 1300 may be easily interchanged to facilitate measurement of any desired wavelength range. The receiving fibers may be connected to a spectrometer for spectral analysis.

Figure 14A:
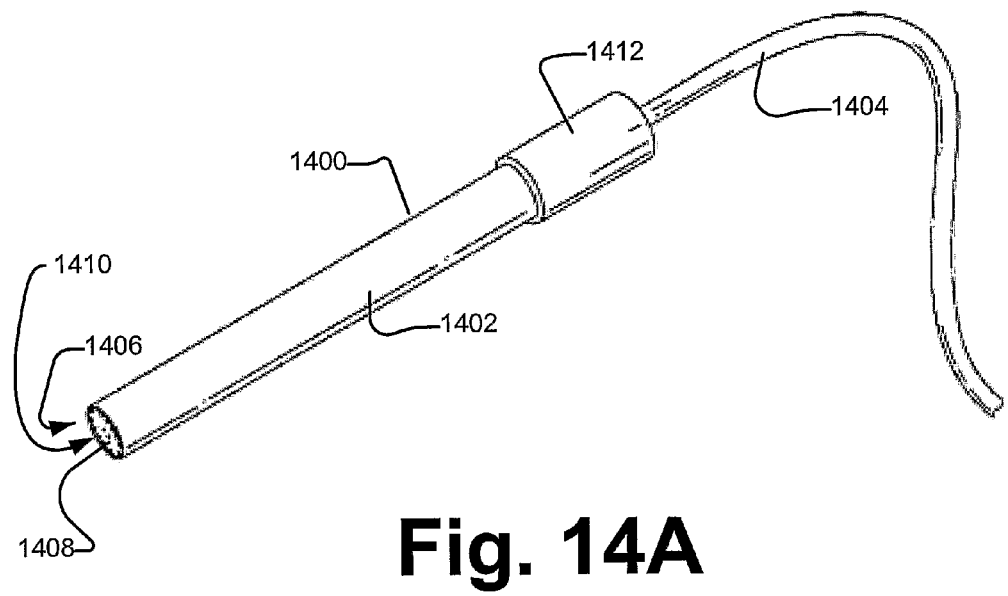
FIG. 14A is an isometric view of an in vivo optical probe.
Figure 14B:
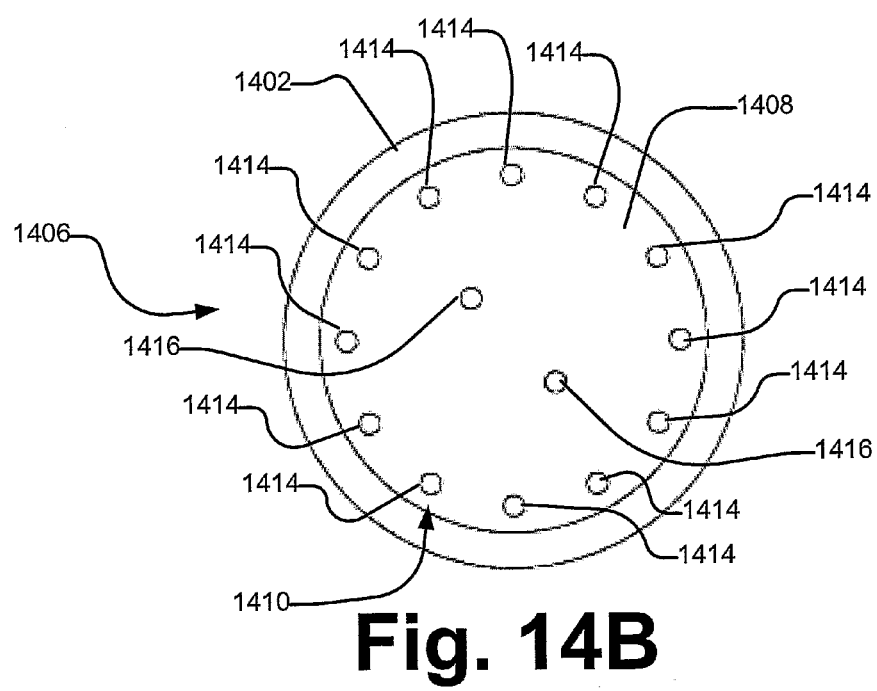
FIG. 14B is a left end elevation view of the optical probe of FIG. 14A.
Figure 15A:
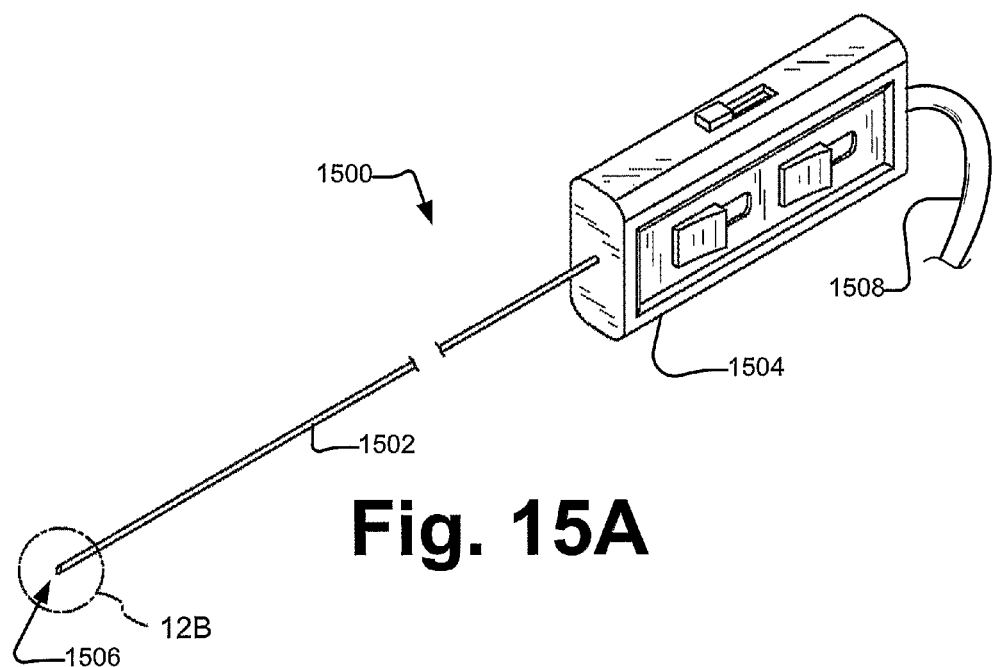
FIG. 15A is an isometric view of an optical biopsy needle.
Figure 15B:
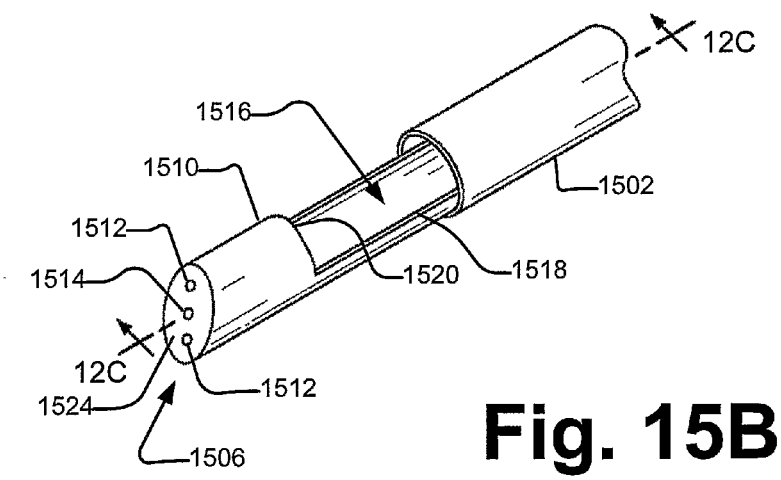
FIG. 15B is an enlarged detail view of a distal tip of the optical biopsy needle as indicated in FIG. 15A.

The system is useful for in situ, real-time diagnosis and identification of prostatic carcinomas. In one embodiment, an optical scanning probe 1400 as shown in FIGS. 14A and 14B may be used to investigate prostate tissue. As shown, the probe 1400 is primarily composed of a tubular shaft 1402 terminating distally with a distal tip 1406. The tubular shaft 1402 is preferably 1 cm or less in diameter. However, the diameter of such a probe may vary depending on choice of material, and the wall thickness necessary to withstand pressures and stress levels within the rectal cavity.

The tubular shaft 1402 houses a plurality of optical fibers 1410 that protrude through an outer end wall 1408 of the tubular shaft 1402 at the distal tip 1406 such that the distal ends of the optical fibers 1410 are flush with the end wall 1408 of the tubular shaft 1402. The optical fibers 1410 extend proximally through the tubular shaft 1402 to a proximal cap 1412, which joins a cable 1404 to the tubular shaft 1402. The cable 1404 provides sheathed protection to the optical fibers 1408 as they extend proximally from the probe 1400 to connect the probe 1400 to attached analytical equipment, for example, a spectrometer.

In one implementation, the probe 1400 design comprises fourteen fibers as shown in FIGS. 14A and 14B, which include twelve transmitter fibers 1414 distributed about the perimeter of the end wall 1408 and two detector fibers 1416 positioned adjacent the center of the end wall 1408. Arrangement of the fibers 1410 may be varied and numbers of each of the transmitter fibers and receiver fibers can be greater or lesser. The output of a light source may be routed to the probe 1400 and controlled by the control circuitry, for example, as shown in FIGS. 8, 12, and 13. The transmitter fibers 1414 may thus be illuminated collectively or individually, in sequence or in groupings, and the detector fibers may be read.

An optical scanning procedure for the diagnosis of prostate cancer and periodic follow-up evaluation of the prostate gland may be performed using the probe 1400 of FIGS. 14A and 14B. Measured spectra provide a gross overview of a large volume of tissue, allowing for easier and faster scanning of the entire prostate gland. This information can be utilized in several different ways to manage the disease: 1) to guide prostate needle biopsies to morphologically adverse locations; 2) to provide comprehensive information during radical prostatectomy surgery regarding tumor margins, particularly capsule, perforation and local metastasis; 3) to deliver therapeutic agents directly to prostatic cancer foci; and 4) to monitor the response to various therapeutic modalities. Some specific clinical applications include prostate biopsies, brachytherapy, cryotherapy, detection of residual and recurrent disease.

Sufficient depth of light penetration (2-4 cm) and a wide field of view for the probe 1400 are obtained by selecting source fibers with small numerical apertures (NA<0.2) and receiver fibers with high numerical apertures (NA>0.5). Intensity modulation of the sources and homodyne demodulation at the output of a fast spectrometer may be used to estimate phase and amplitude variations. The phase and amplitude modulations are then used to determine both the scattering coefficient and the location of a lesion responsible for a scattering event.

In another embodiment, a minimally invasive automatic optical biopsy needle 1500 as shown in FIGS. 15A-15E is used in the diagnosis of prostate cancer. An optical biopsy needle 1500 incorporates an integrated optical probe. The invasive optical biopsy needle 1500 may be designed to capture ESS and fluorescence spectra of prostatic tissues in the range of 200-1,150 nm. The optical biopsy needle 1500 is composed primarily of a long outer sheath 1502 attached to an actuator handle 1504. The outer sheath 1502 houses an inner needle 1510 (see FIGS. 15B and 15C) that is actuated by the actuator handle 1504. A cord sheath 1508 extends proximally from the actuator handle 1504 to couple the optical biopsy needle 1500 to analytical equipment as further described below.

The distal tip 1506 of the inner needle 1510 forms and angled blade 1524 to assist in the ability of the inner needle 1510 to puncture through tissue. Initially, the inner needle 1510 is substantially housed within the outer sheath 1502 with only the angled blade 1524 extending beyond the distal end of the outer sheath 1502. The actuator handle 1504 causes the inner needle 1510 to extend distally from the distal end of the outer sheath 1502 to collect a tissue sample 1522 in the standard manner of biopsy needles. The inner needle 1510 defines a recessed tray area 1516 defined by low sidewalls 1518 spaced proximally from a distal tip 1506 of the inner needle 1510. The inner needle 1510 also defines a barb 1520 at the top surface of the inner needle 1510 at the distal end of the recessed tray area 1516 extending proximally toward the recessed tray area 1516. The barb 1520 assists in extracting and securing a tissue sample 1522 within the recessed tray area 1516. A typical tissue core sample 1522 may be approximately 15 mm long for each biopsy.

The inner needle 1510 may be engineered to bring a plurality of optical fibers 1512, 1514 from the actuator handle 1504 to the distal tip 1506 flush with the blade 1524 surface as shown in FIGS. 15C-15E. In one exemplary embodiment, a 16-gauge outer sheath 1502 may house a 20-gauge inner needle 1510. Three 100-200 µm fibers, one transmitter fiber 1514 and two receiver fibers 1512 may be threaded through conduits formed within the inner needle 1510. Other embodiments may incorporate needles and sheaths of greater or lesser gauge or alternate numbers and diameters of fibers. Excitation of tissue is preferably restricted to the sample point. A small numerical aperture (circa 0.2 or less) may be used for the transmitter fiber 1514 to ensure that the excitation does not spread too much over the propagation distance. Larger numerical apertures are preferably used for the receiver fibers 1212 in order to maximize the pick-up.

As shown in FIG. 15D, the optical fibers 1512, 1514 travel underneath the recessed tray area 1516 to the distal tip 1506 of the inner needle 1510. The terminal ends of the optical fibers 1512, 1514 are positioned flush with the blade surface 1524 of the inner needle 1510 and are exposed therein. The terminal ends of the optical fibers 1512, 1514 may be spaced apart about the blade surface 1524. In an exemplary embodiment as shown in FIG. 15E, the optical fibers 1512, 1514 may be arranged in a vertical row with the transmitter fiber 1514 flanked above and below by receiver fibers 1512. Other patterns of arrangement for the optical fibers 1512, 1514 are possible and greater or fewer fibers may be used. The optical fibers 1512, 1514 extend proximally through the inner needle 1510 and the actuator handle 1504 and exit the actuator handle 1504 through the cord sheath 1504. The cord sheath 1508 provides protection to the optical fibers 1512, 1514 as they extend proximally from the actuator handle 1504 to attached analytical equipment, for example, a spectrometer.

In actual practice, the optical biopsy needle 1500 may be inserted into the prostate gland at the desired location and signal normalization performed before activating the light source. The distal tip 1506 of the inner needle 1510 is positioned inside the prostate. The receiver fibers 1512 collect the diffuse reflectance and fluorescence emissions from the tissue under excitation generated by the transmitter fiber 1514. Fluorescence and reflectance measurements are then taken to determine whether the adjacent tissue is benign or malignant. Tissue sample collection may thus be limited to areas of tissue that appear to be abnormal based upon spectral analysis. This procedure is repeated each time and biopsy samples will be taken from several locations of the prostate.

The presence of blood may restrict the collection region to a fairly thin layer next to the tissue surface. A strategy for limiting the range of excitation may be to choose a spectral range where the signal does not propagate too far into the material, yet still has a large enough scattering coefficient in order to return some signal. The spectral range is selected with particular attention to the absorption coefficient where it will be appreciated that the scattering coefficient does not vary appreciably with wavelength from visible to near infrared (NIR). The absorption coefficient, however, does. Absorption is much larger in the near UV and the blue than in the red and NIR. Higher absorption leads to higher fluorescence that contains more usable information. Therefore, a suitable wavelength range may be in the visible range with one or more excitation signatures below 400 nm.

5. Examples

The above-described techniques have been tested on a number of different samples, the results for which are summarized in FIGS. 16-19B.

a. Example 1

Figure 16:
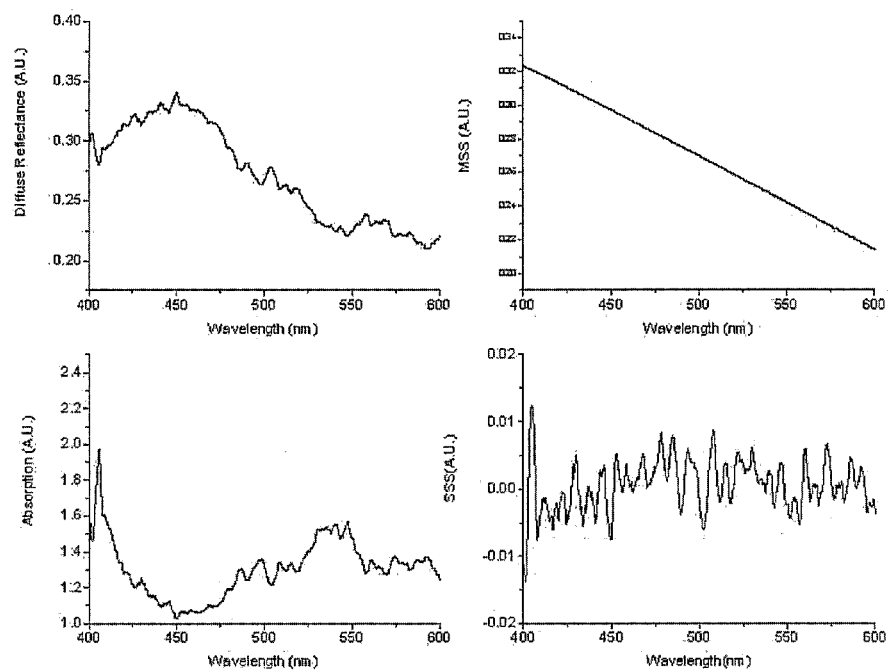
FIG. 16 provides illustrative results using a first sample.

Results are provided in FIG. 16 for application of the above-described method to a sample of white wax. Wax has a consistency similar to that of biological tissue. The samples were prepared by coating slides with the wax, with the thickness estimated to be on the order of fractions of a millimeter. The results are presented as four plots, showing the diffuse reflectance, absorption, and multiple and single scattering functions as determined from the diffuse reflectance. In this instance, the fluorescence was negligible.

b. Example 2

Figure 17:
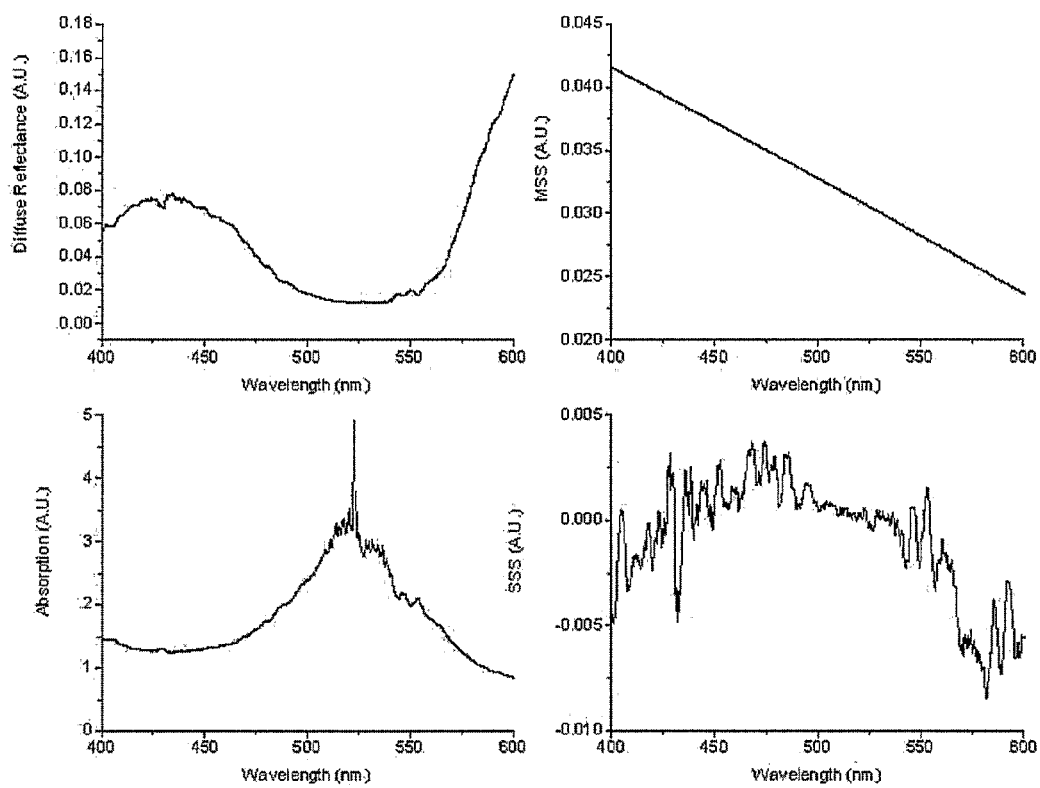
FIG. 17 provides illustrative results using a second sample.

Results are provided in FIG. 17 for application of the above-described method to a sample of red wax. Again, the samples were prepared by coating slides with the wax, with the thickness estimated to be on the order of fractions of a millimeter. The results again show the diffuse reflectance, absorption, and multiple and single scattering functions as determined from the diffuse reflectance.

c. Example 3

Figure 18A:
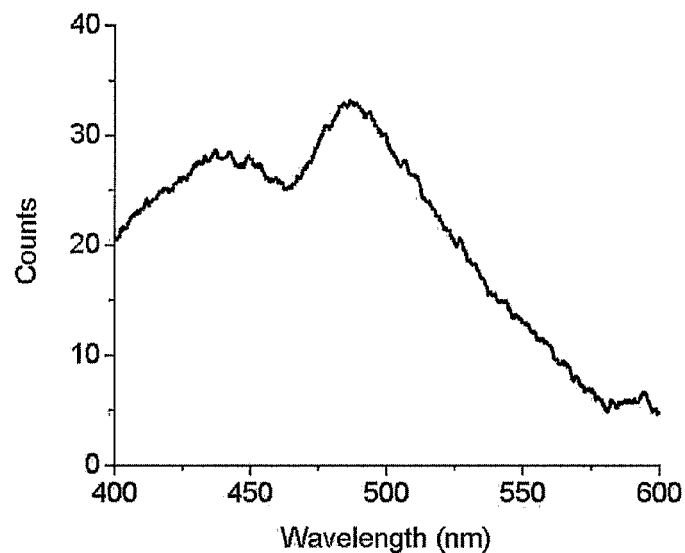
FIGS. 18A and 18B provide illustrative results using a third sample.
Figure 18B:
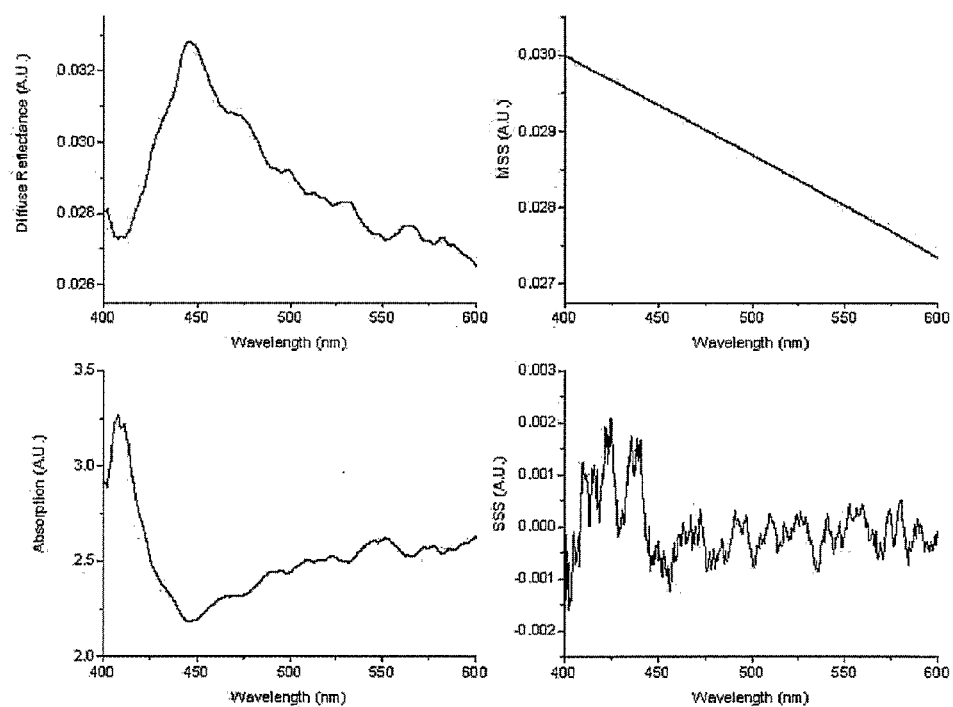

Results are presented in FIGS. 18A and 18B for a 10-µm-thick layer of prostate tissue preserved in formalin and mounted in paraffin. FIG. 18A shows the measured fluorescence and FIG. 18B shows results after application of the above-described methods, namely the diffuse reflectance, absorption, and multiple and single scattering functions as determined from the diffuse reflectance.

d. Example 4

Figure 19A:
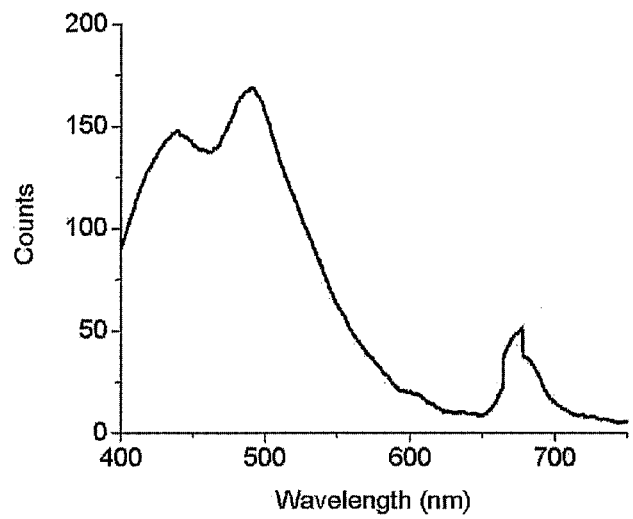
FIGS. 19A and 19B provide illustrative results using a fourth sample.
Figure 19B:
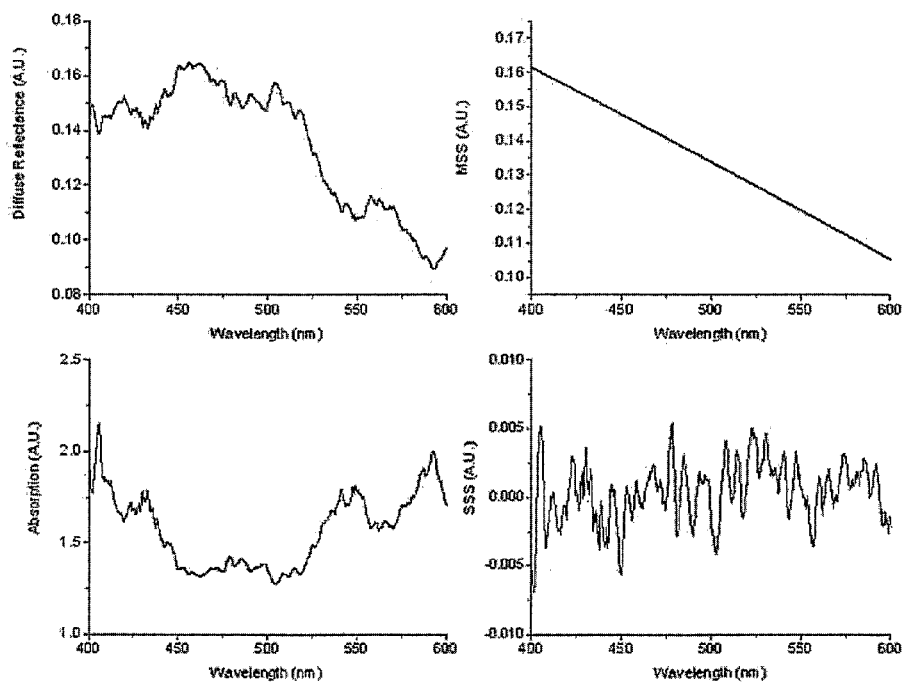

Results are presented in FIGS. 19A and 19B for a cucumber sample having a thickness believed to be on the order of fractions of a millimeter. Cucumber is much like human tissue except that the cell walls are thicker. FIG. 19A shows the measured fluorescence and FIG. 19B shows the results for the diffuse reflectance, absorption, and multiple and single scattering functions. Three fluorescent lines are evident in the results of FIG. 19A and are believed to correspond to collagen, NADH, and chlorophyll (in the red portion of the spectrum).

e. Example 5

The fifth example provides results derived from application of the above-described methods and systems on three different types of oral mucosa fixed in formalin and mounted in paraffin in 20-μm sections onto standard microscope slides. Three different slide classifications were made, based on the condition of the oral tissue on the slide: hyperkeratosis, dysplastic, and squamous cell carcinoma. In the results presented in FIGS. 20-22, discussed in detail below, these classifications are identified by the letters "H," "D," and "SCC" respectively. The tissue slides were placed in an optical mount and a probe was used to excite the tissue electromagnetically as described above, and data were collected.

Figure 20:
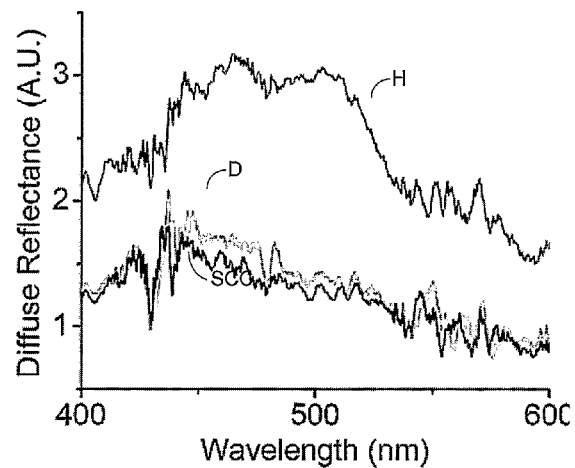
FIG. 20 provides a graph of diffuse reflectance extracted from three oral mucosa samples.

The EEM generated from each tissue sample was broken up into diagonal and off-diagonal elements as described above, and the diffuse reflectance obtained from the diagonal elements. The diffuse reflectance generated by each of the three different tissue samples is illustrated in FIG. 20. The off-diagonal elements for the samples are illustrated with the other information extracted from the diagonal elements in FIG. 21. The diffuse reflectance from the diagonal elements of the EEM was processed further to separate out the single scattering contribution SSS, the multiple scattering contribution MSS, and the absorption. The three elements extracted from the diagonal, along with the off-diagonal elements of the EEM for each tissue sample, are illustrated in FIG. 21.

Figure 21:
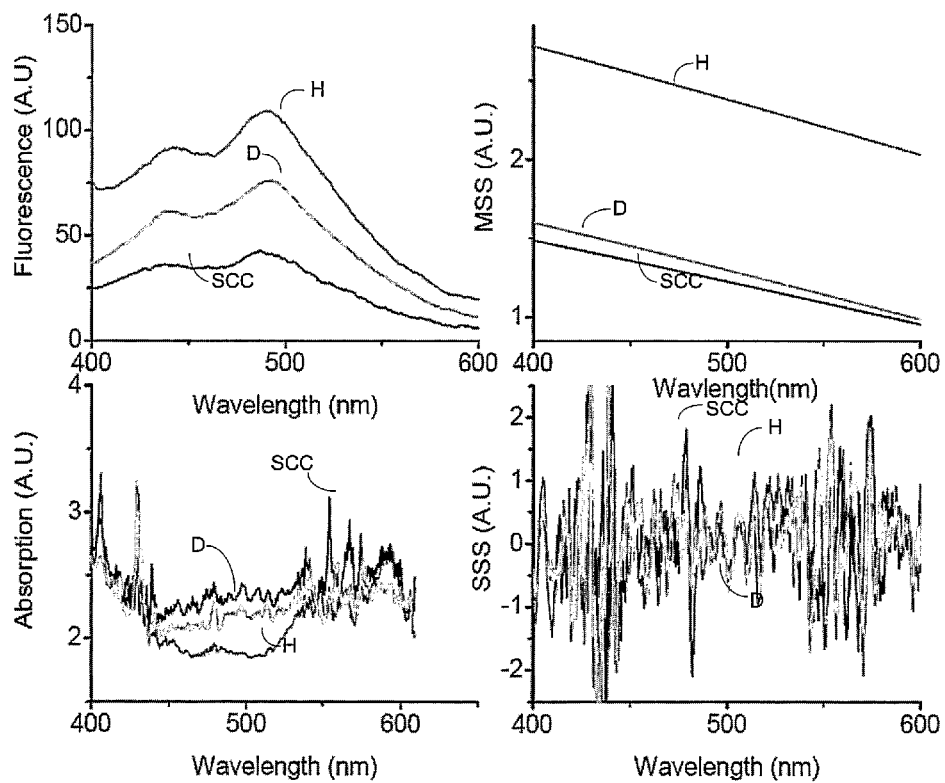
FIG. 21 provides extracted portions of an excitation emission matrix corresponding to data of FIG. 17.
Figure 22:
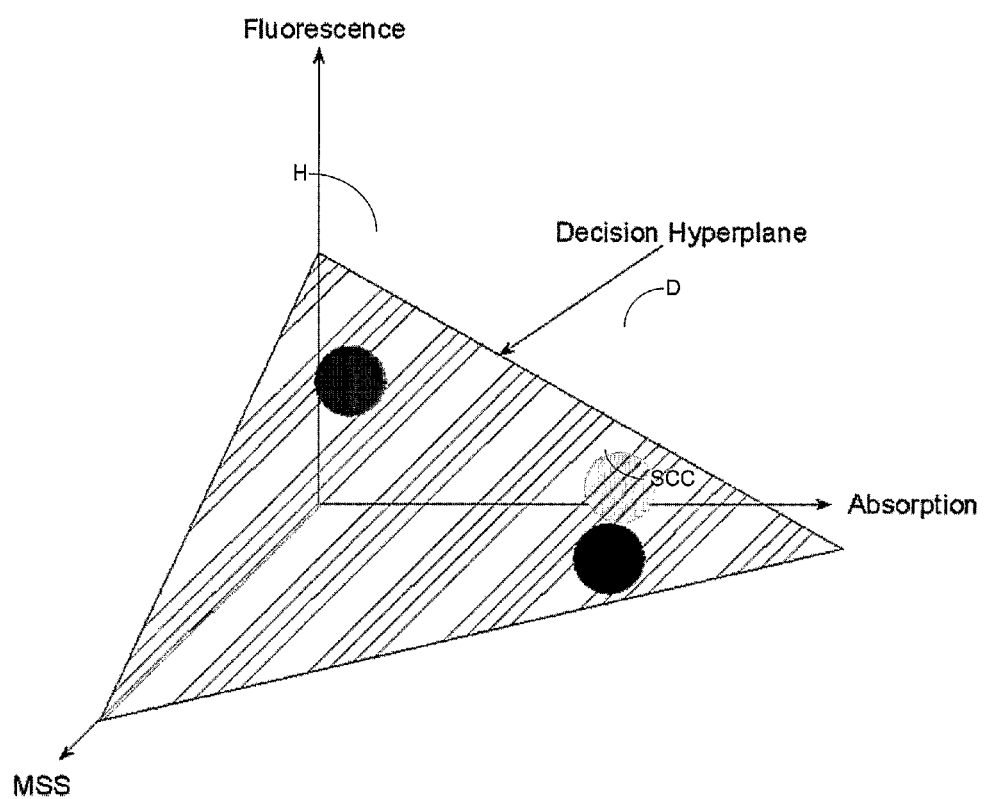
FIG. 22 provides an example of a decision hyperplane that may be used for separation of differently characterized tissue.

From FIG. 21 it is clear by visual inspection for this example that there are between one and three features that can be used in the decision space to distinguish between hyperkeratosis and the other two classifications. The primary features that can be differentiated are the overall integrated levels of the MSS, fluorescence, and absorption characteristics. These characteristics may be used to form a multidimensional space, in this particular instance a three-dimensional space, with features in the plane defining discriminatory aspects of the characteristics. In particular, for this example, FIG. 22 shows such a space, with a plane drawn in the plane that separates the hyperkeratosis case from the others.

While this example permits the decision plane to be determined from visual inspection of the elements separated from the EEM, this may not be true generally, particularly in instances where more samples are processed and the number of characteristics is larger. In such instances, embodiments of the invention may use principle constituent analysis and pattern-recognition techniques to determine the decision space and the decision hyperplane.

f. Example 6

The sixth example provides results of automated tissue classification. The data were collected and analyzed using a system represented schematically in FIG. 23. The system 2304 uses a probe to acquire spectral data from a non-stained 20-μm sample of tissue 2308 and a microscope imaging system for obtaining images of a region with a 5-μm hematoxylin and eosin stained slide 2312. The image 2316 is used to generate an EEM using the methods described above in connection with FIG. 6. The application of cluster programs to the spectral measures derived from the EEM permits classification of the image to generate a decision map 2320 that characterizes a spatial region of the complete image 2324 as having normal, dysplastic, or cancerous tissue.

Figure 24A:
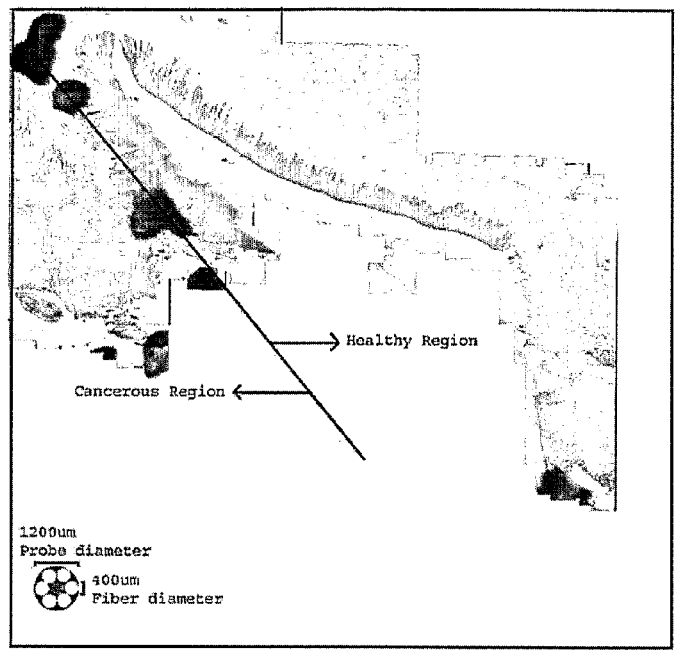
FIGS. 24A-24E provide results of an analysis of a first tissue sample using the arrangement of FIG. 20.
Figure 24B:
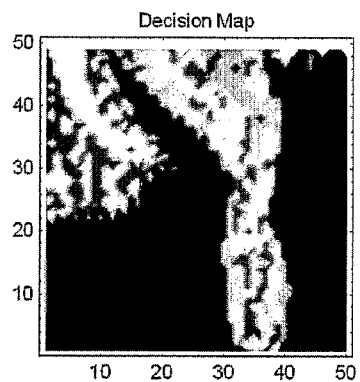
Figure 24C:
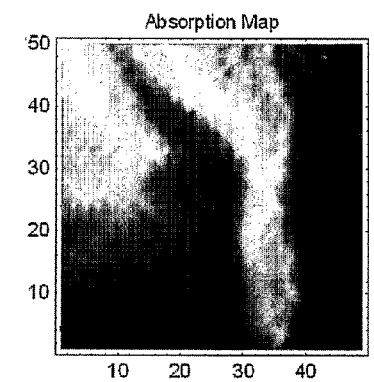
Figure 24D:
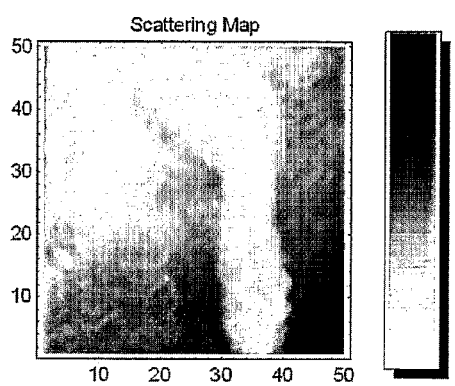
Figure 24E:
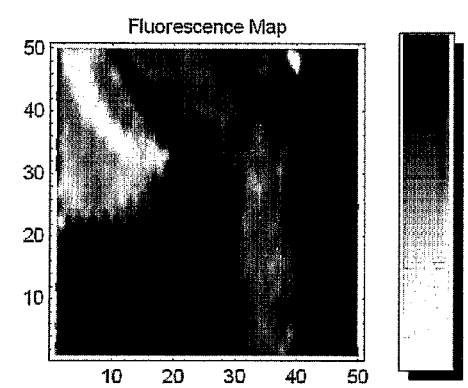
Figure 25A:
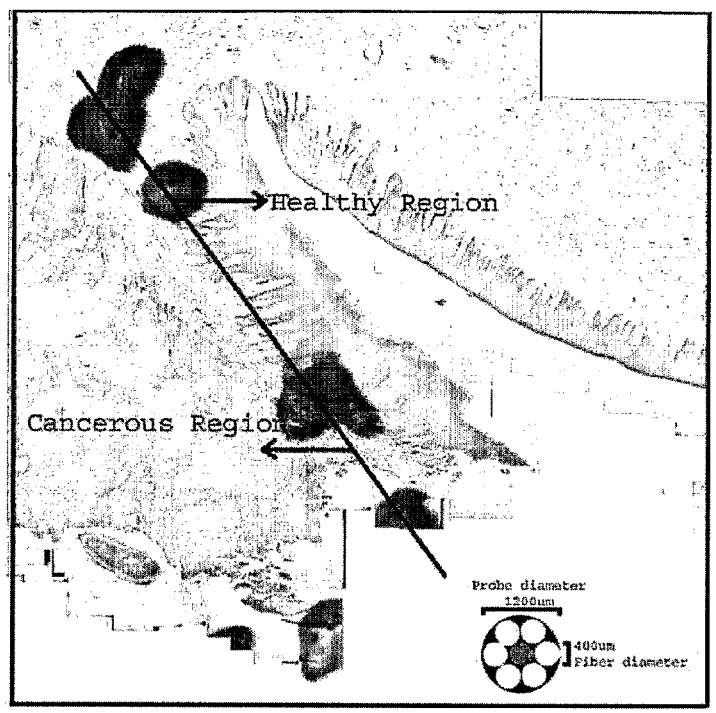
FIGS. 25A-25E provide results of an analysis of a second tissue sample using the arrangement of FIG. 20.
Figure 25B:
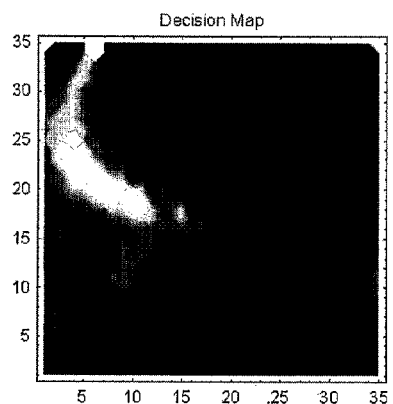
Figure 25C:
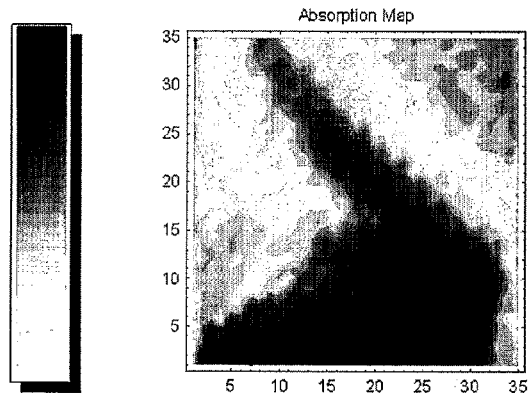
Figure 25D:
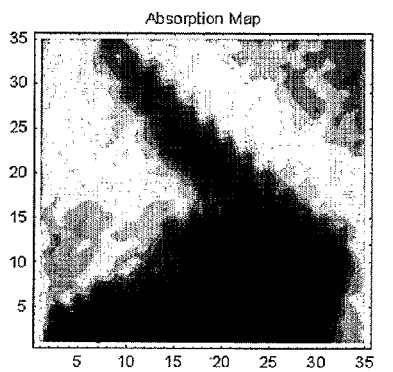
Figure 25E:
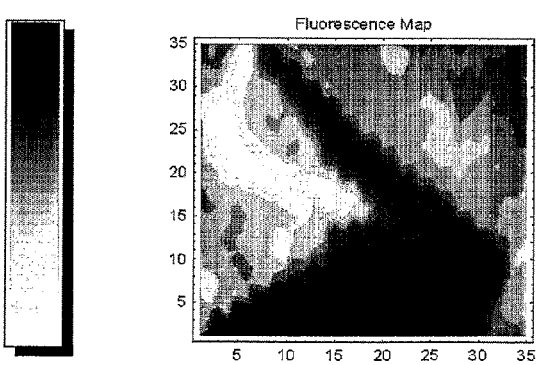

One illustration for these results is provided in FIGS. 24A-24E. FIG. 24A provides a micrograph of the tissue sample, delineating healthy and cancerous regions. Results of the application of the method of FIG. 6 to this tissue sample are provided in FIGS. 24C-24E to show maps of the absorption, scattering, and fluorescence respectively. FIG. 24B shows the decision map that results from the classification of the tissue after performing the cluster analyses. Measurements were made using a probe having a plurality of 400-μm fibers to provide a total probe diameter of 1200 μm. Cancerous tissue is identified in the decision map by white regions, with grayscale regions identifying dysplastic and normal tissue. The presence of cancerous tissue in the cancerous region is confirmed by the analysis.

g. Example 7

Figure 23:
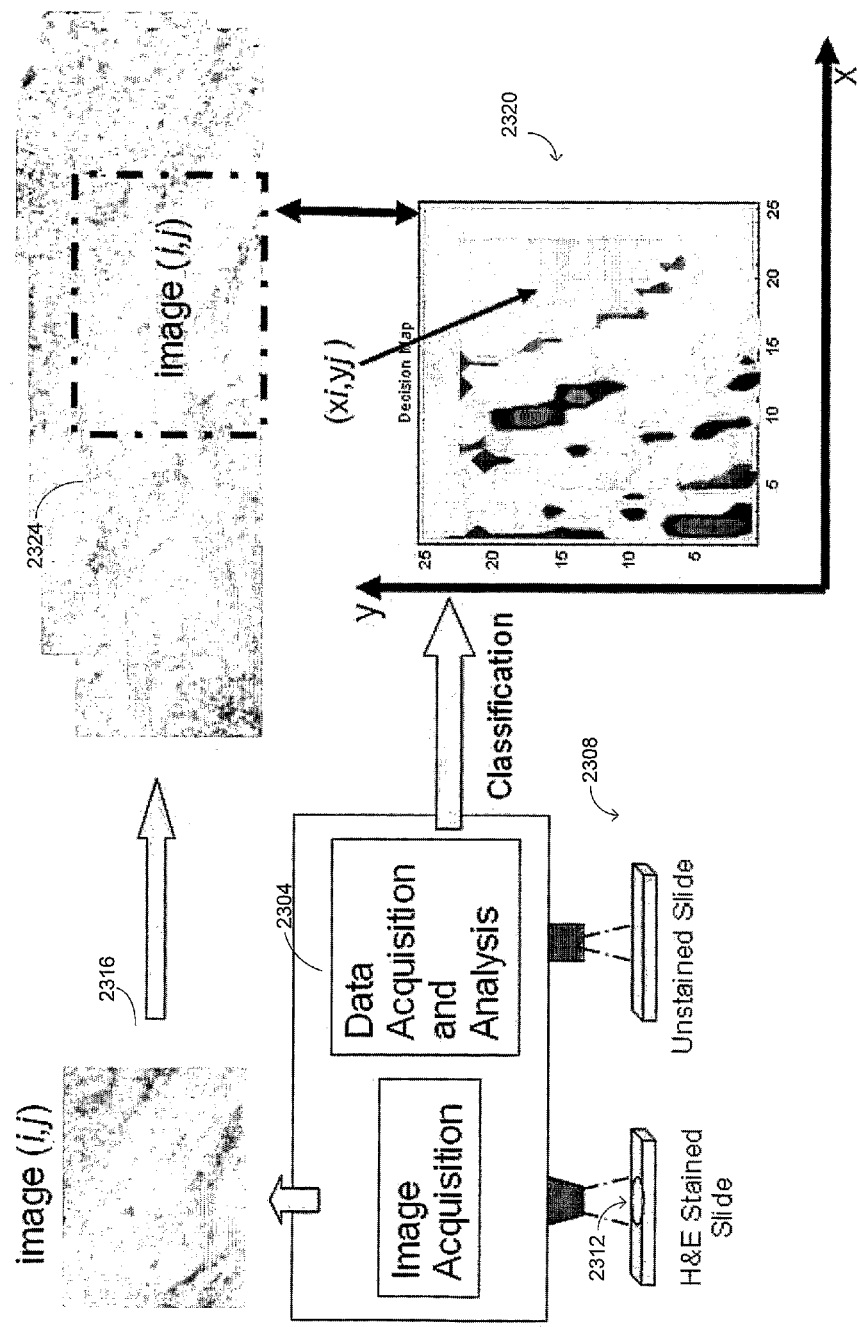
FIG. 23 provides a schematic representation of an arrangement used to collect data in certain examples.

The seventh example provides results similar to those of FIGS. 24A-24E and also result from application of the method of FIG. 6 using the system of FIG. 23. FIGS. 25A-25E have a layout similar to that of FIGS. 24A-24E, with FIG. 25A providing a micrograph of the sample that delineates healthy and cancerous regions, FIG. 25B providing the decision map that results from application of the method, FIG. 25C providing a map of the absorption determined from the EEM, FIG. 25D providing a map of the scattering determined from the EEM, and FIG. 25E providing a map of the fluorescence determined from the EEM. Again, the results in the decision map show consistency with the automated classifications of tissue type made by application of methods of the invention.

h. Example 8

Absorption Spectra of Prostatic Tissue

Figure 26:
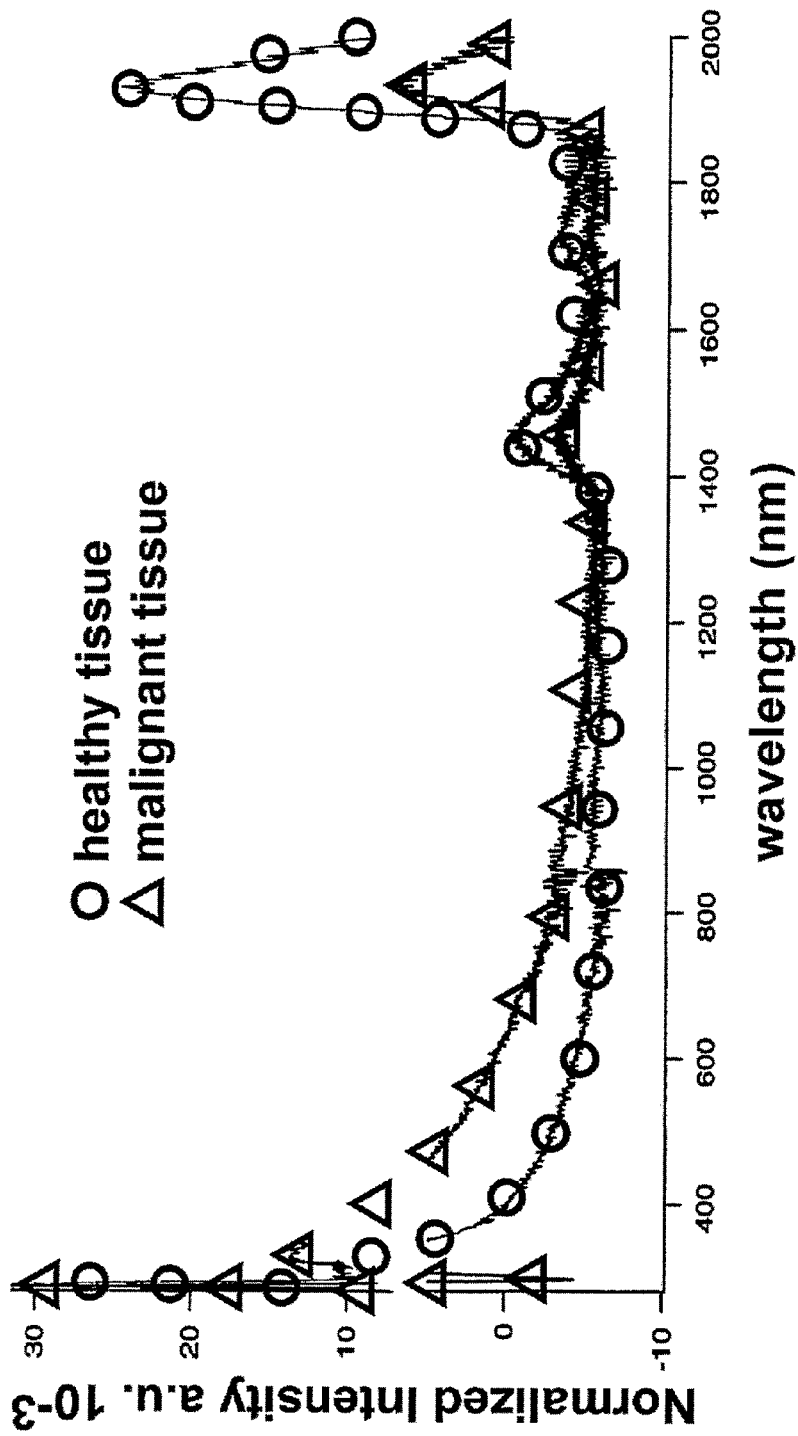
FIG. 26 is a graph depicting the absorption spectra of both healthy and cancerous prostatic tissue.

Absorption spectra analyses were performed on both healthy and malignant prostatic tissues using a Perkin Elmer absorption spectrometer at the National Institute of Standards and Technology in Boulder, Colo. The healthy tissues were obtained from a twenty-year-old donor who had no previous history of prostatic diseases. The carcinoma tissue samples were obtained from a radical retropubic prostatectomy (RRP) specimen immediately after the surgery. The frozen samples were placed on slides and OCT sealant was applied. No staining was used. A trained pathologist identified the cancer areas of the tissues samples. The results, illustrated in the graph of FIG. 26, reveal a number of spectral features that are common to spectra of both healthy and malignant prostatic tissues as well as unique features. The amplitudes of the features vary systematically, with an intensity reversal occurring around 1400 nm. However, these spectral features lie in the region where absorption due to water is very high and hence are unsuitable for in vivo diagnostics.

i. Example 9

Fluorescence Spectra of Prostatic Tissue

As there is no published data regarding fluorescence spectra of prostatic tissue, a preliminary measurement using formalin-fixed, paraffin-embedded prostate tissue was undertaken. Using a pen, a pathologist marked prostate cancer and normal areas on a collection of haematoxylin and eosin (H&E) stained whole-mount slides. Optical measurements were taken from unstained 10 μm thick sections cut from each block adjacent to the H&E section. By carefully overlaying the pathologically classified areas on H&E slides with the corresponding unstained section, auto-fluorescence spectra were generated for normal and malignant prostatic tissue from two different patients, as illustrated in FIGS. 27A and 27B. The excitation source was a violet light emitting diode (LED) with an optical bandwidth of 360-410 nm and 25 μW power. Both types of tissue appear to display collagen and nicotinamide adenine dinucleotide (NADH) peaks approximately located at wavelengths of 440 nm and 490 nm, respectively.) However, fluorescence intensity levels of these fluorophores obtained from formalin-fixed tissue are much lower compared to those from fresh in vivo or ex vivo tissue samples. Therefore, the fluorescence intensities measured from formalin-fixed tissue are not useful references in clinical settings.

j. Example 10

Fluorescence Spectral of Prostate Cell Cultures

To identify specific endogenous fluorophores and their excitation and emission spectra useful in clinical settings to diagnose prostatic carcinoma in vivo, experiments may be performed using a collection of prostate cancer cell lines. An appropriate collection should be comprehensive and include prostate cell cultures that represent benign cells, cancer, and metastatic disease. The collection should constitute a variety of different types and stages of prostate cancer, while also reflecting the heterogeneous nature of this malignancy. Exemplary prostate carcinoma cell lines may include LNCaP, DU 145, NCI-H660, PC-3, ALVA-31, 22Rv1, CWR-R1, DuCaP, LAPC-4, MDA PCa 1, MDA PCa 2a, MDA PCa 2b, PC-346C, PSK-1, and VCaP, as well as BPH-1 and PrEC primary cultures of normal prostate to generate fluorescence spectra. Rhodamine-B spectra may be used to normalize between different experiments.

Cell suspensions may be prepared and placed in a quartz cuvette with 1 cm path length. A conventional laboratory fluorometer (e.g., Fluorolog-3, JY Horiba Inc., Edison, N.J.) may be used to characterize the fluorescence properties of each cell suspension. An exemplary fluorometer instrument may consist of a 450 W xenon arc lamp, double excitation and emission scanning monochromators, a sample compartment with a cuvette holder and magnetic stirrer, and a photomultiplier tube (PMT). Adjustable parameters of the instrument may include the excitation and emission wavelength ranges and increment, the excitation and emission band-passes, the high voltage of the PMT, the integration time, the stirring speed of the magnetic stirrer, and the collection geometry.

Fluorescence excitation-emission matrices may be recorded by measuring the fluorescence-emission spectra over a range of excitation wavelengths. A fluorescence EEM involves measurement of the fluorescence intensity as a function of both excitation and emission wavelengths. The excitation wavelength may be varied from about 260 to 540 nm. At each excitation wavelength, fluorescence emission spectra may be recorded from a wavelength slightly above the excitation wavelength to 700 nm. These wavelength ranges will enable characterization of all endogenous fluorophores, porphyrins, ceroid, tryptophan, NAD(P)H and FAD, likely to be present in prostate cells in the ultraviolet (UV) through visible (VIS) spectrum.

Figure 28:
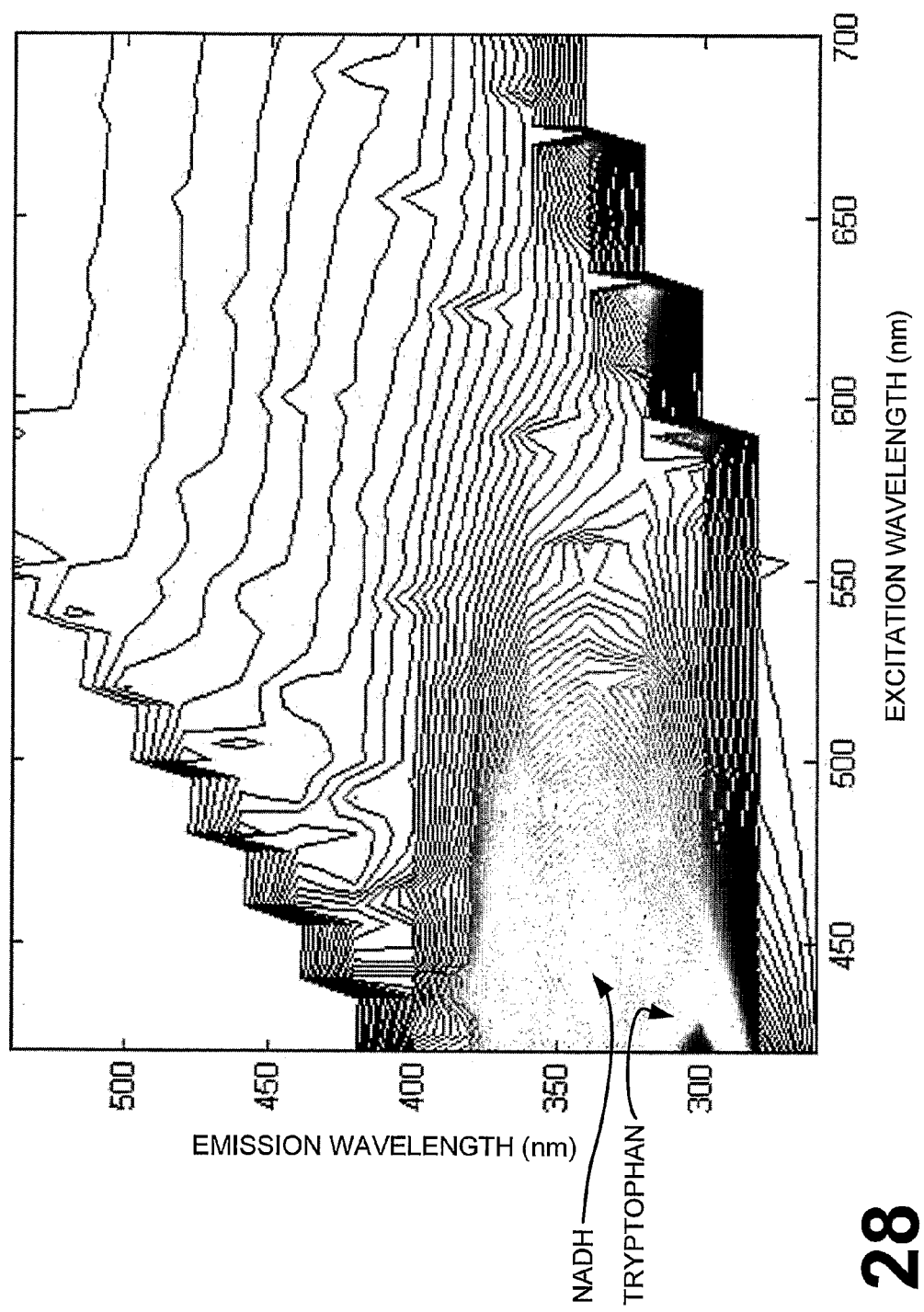
FIG. 28 is a contour plot of excitation vs. emission wavelengths for a DU145 malignant prostate cell suspension.
Figure 29:
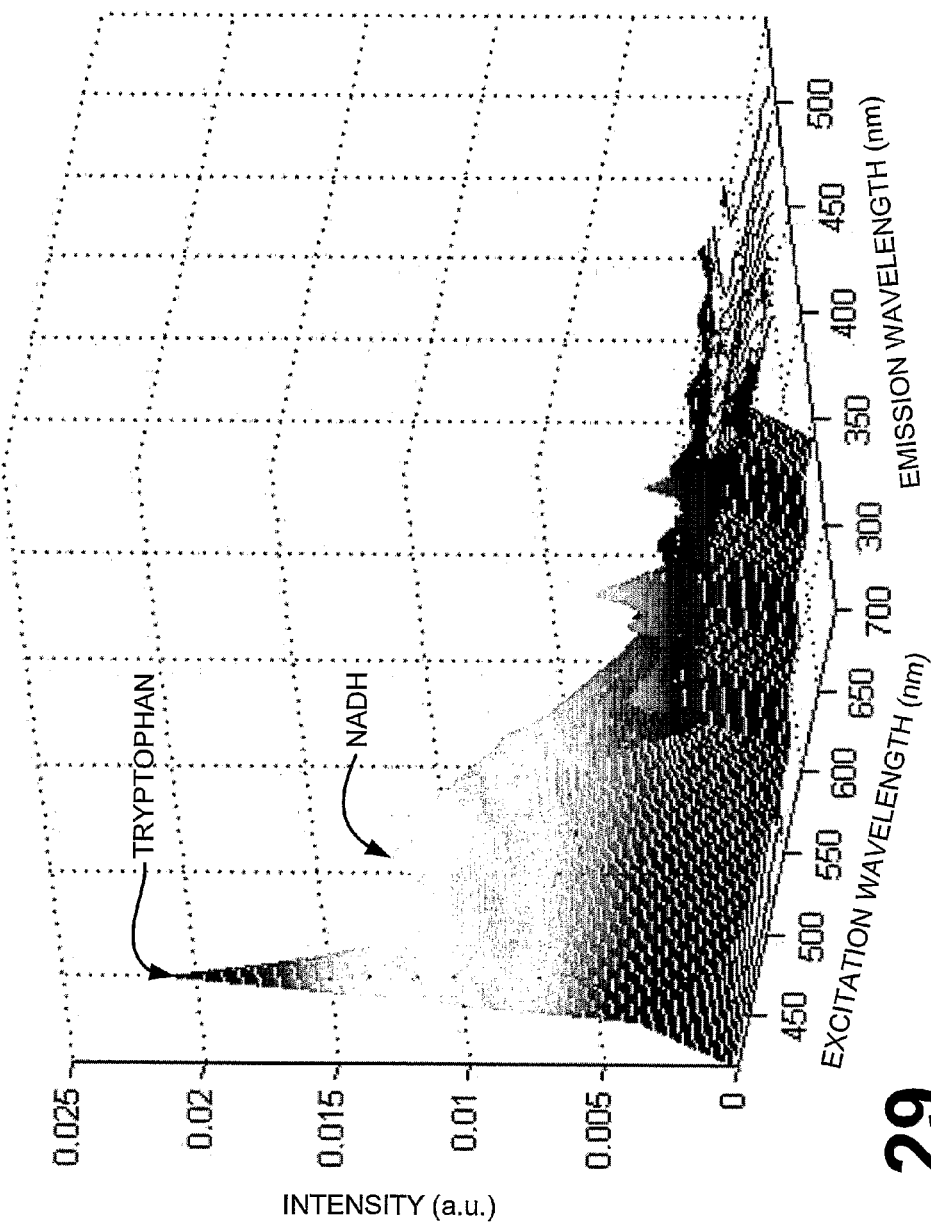
FIG. 29 is a three-dimensional plot of intensity vs. excitation wavelength vs. emission wavelength for a DU145 malignant prostate cell suspension.

FIG. 28 and FIG. 29 illustrate EEM matrix data obtained for a DU145 cell suspension (3 million cells/mil) using Fluorolog-3. The excitation-emission frequencies of NADH and Tryptophan are known and the amounts present in benign tissue are relatively higher than in malignant tissue. The fluorescence signal is proportional to the concentrations of each fluorophore. For a DU145 cell suspension, the peak fluorescence intensity due to tryptophan (0.02 a.u.) is two-fold higher than for NADH (0.01 a.u.).

Figure 30B:
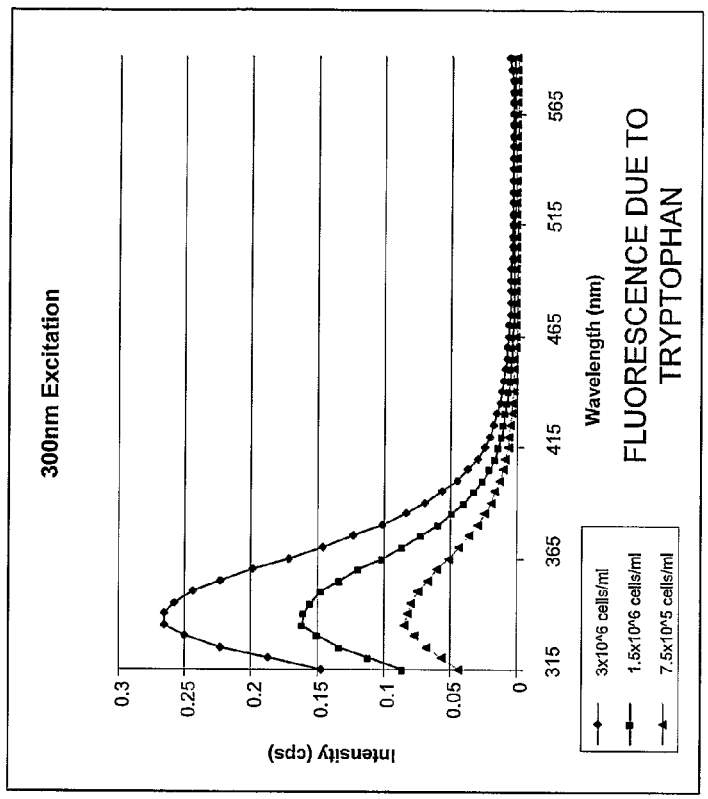
FIG. 30B is a graph depicting the intensity of fluorescence from tryptophan of a DU145 malignant prostate cell suspension upon excitation by light at a wavelength of 300 nm.
Figure 30A:
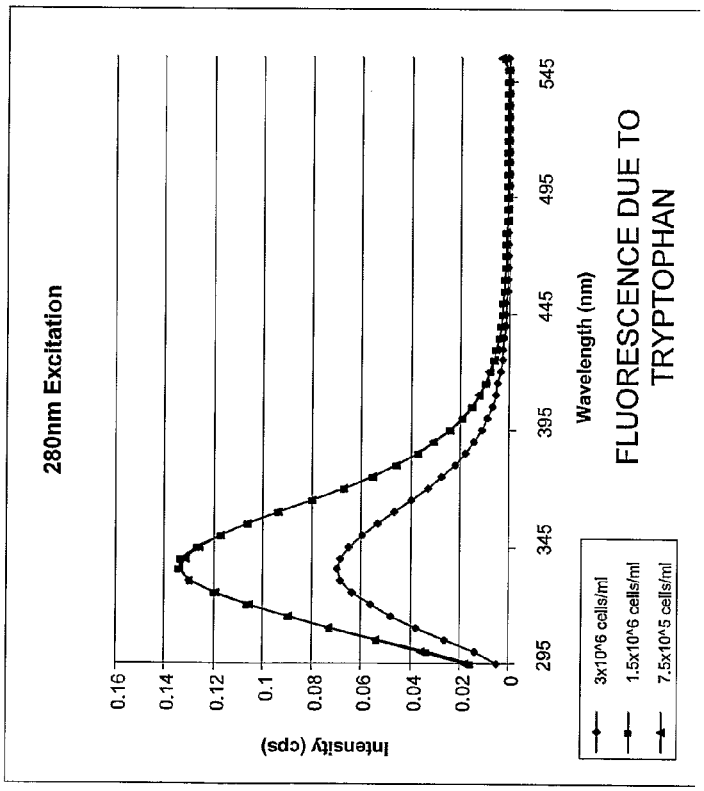
FIG. 30A is a graph depicting the intensity of fluorescence from tryptophan of a DU145 malignant prostate cell suspension upon excitation by light at a wavelength of 280 nm.
Figure 31A:
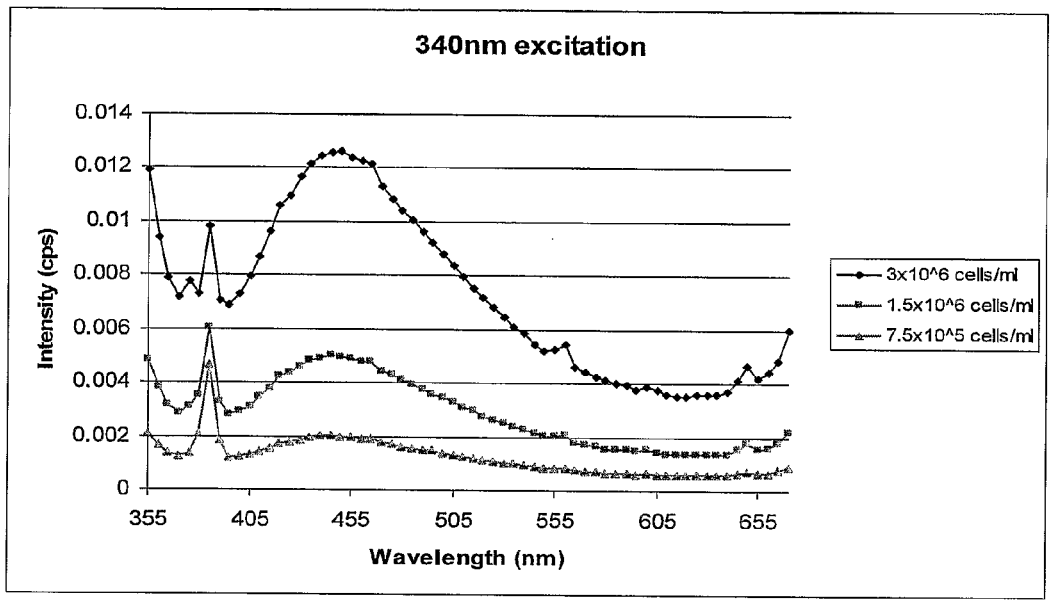
FIG. 31A is a graph depicting the intensity of fluorescence from NADH of DU145 malignant prostate cell suspension upon excitation by light at a wavelength of 340 nm.
Figure 31B:
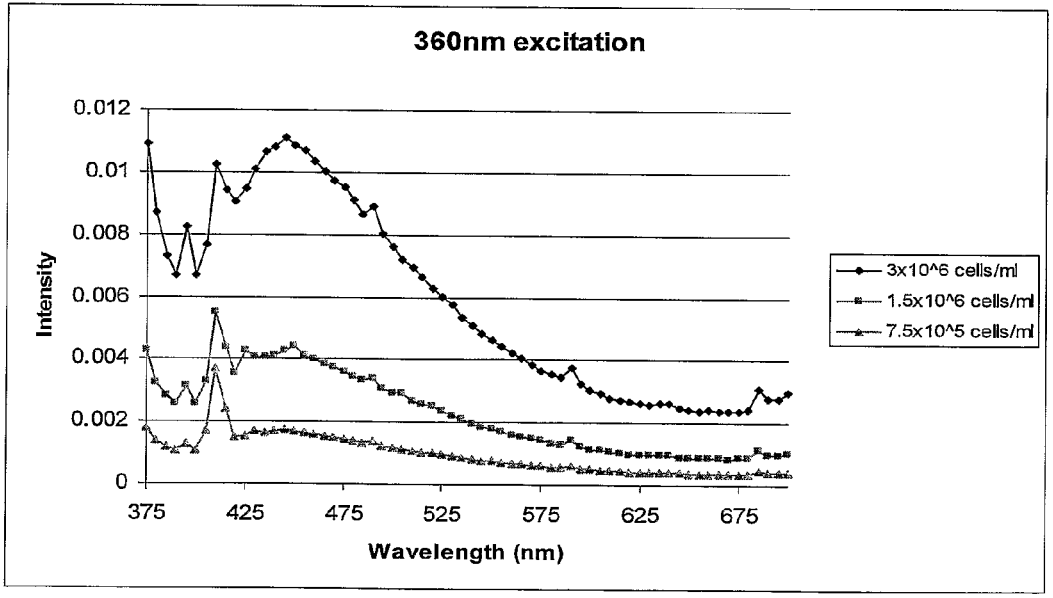
FIG. 31B is a graph depicting the intensity of fluorescence from NADH of DU145 malignant prostate cell suspension upon excitation by light at a wavelength of 360 nm.

The peak fluorescence intensity for each fluorophor is determined by absorption/absorbers of the medium. For example, fluorescence from tryptophan for three different cell concentrations at wavelengths of 280 and 300 nm excitations is indicated, respectively, in FIGS. 30A and 30B. FIGS. 31A and 31B indicate fluorescence from NADH for three different cell concentrations at wavelengths of 340 and 360 nm, respectively. The peak fluorescence intensity of tryptophan for the highest cell concentration (6 million cells) is lower at 280 nm than the two lower concentrations (1.5 and 0.75 million cells). The order is reestablished, however, at 300 nm excitation. This is likely caused by an absorption feature at 280 nm and hence the absorption and scattering coefficients of the medium need to be measured to extract the "intrinsic" fluorescence spectrum.

In addition if there are non-fluorescing absorbers, then those will reduce the excitation energy at the focal volume and reduce the amount of fluorescence that reaches the detector. The larger the concentration of absorbers, the greater the reduction of excitation energy. This is called "trapping." Consequently, scattering and absorption coefficients of cell cultures need to be evaluated to recover the fluorescence signal. This is also true for tissue. Absorption is even more pronounced in biological tissue due to oxy- and deoxy-hemoglobin. An integrating sphere and a cuvette may be used to measure absorption and scattering coefficients of biological tissue and cell suspensions.

A statistical analysis was performed to determine whether fluorescence spectrum due to tryptophan is significantly different between normal (BPH-1) and malignant (DU145, PC3, DuCap, VCap) cell suspensions. For each fluorescence spectrum, data points between 3 dB cutoff points were included in the analysis. There was a statistically significant difference in the fluorescence signal due to tryptophan between normal and malignant cell suspensions at 280 and 300 nm excitations (t-test $p<0.0001$). The same was true for NADH at 340 nm excitation (t-test $p<0.0001$). It may be concluded that there is significantly more tryptophan and NADH in normal cells than in malignant cells and these differences may be utilized for tissue classification.

k. Example 11

Diagnosis of Prostatic Pathology Using Optical Probe

An optical probe was used to measure and characterize the prostatic tissue. Using data reductions, normalization, and applying artificial neural networks, identification of malignant prostatic tissue from normal prostatic tissue is demonstrable.

An exemplary invasive optical probe 1400 as shown in FIG. 14 captures ESS of prostatic tissues from ex vivo RRP specimens in the range of 200-1150 nm. Over 900 spectra of prostatic tissues from 52 RRP patients were collected using a 22 gauge optical probe (custom-made by Ocean Optics, Dunedin, Fla.). The optical probe 1100 may be inserted into an 18-gauge biopsy needle to provide in vivo access to the prostate. A tungsten/halogen light source provides illumination over the wavelength range 360-2000 nm. The light source is coupled to a 200 μm optical fiber selected to transmit over the wavelength range of interest. The probe consists of a bundle of 14 optical fibers. There are six UV-VIS (200-750 and six VIS-NIR (450-1100) illumination fibers arrayed around two read fibers, one UV-VIS and one VIS-NIR. The two read fibers are coupled to an Ocean Optics S2000 double spectrometer with CCD detectors. A laptop computer is used to control the system and collect data.

Tissue spectra collected from each location were recorded with a unique identifier providing precise information of the location. After collecting tissue spectra from the near-end of the optical probe, a corresponding biopsy was taken from each location. Each sample was polarized using blue ink to identify the near-end of the biopsy core. The biopsy samples were spot-frozen in OCT compound using a dry ice/isopentane bath for standard pathological classification. After the data collection, RRP specimens were fixed in 10% neutral-buffered formalin (NBF) to generate whole-mount sections.

A trained pathologist may use standard pathological methods to review routine 5 μm H&E stained biopsy specimens. Each of the slides may be evaluated for the presence of carcinoma, denoted by Gleason sum (primary Gleason grade+ secondary Gleason grade), prostatic intraepithelial neoplasia (PIN), acute prostatitis, chronic prostatitis, cystic atrophy, simple atrophy, basal cell hyperplasia, atypical adenomatous hyperplasia, and various subtypes of benign prostatic hyperplasia (BPH) nodules (adenomatous, fibroadenomatous, fibromyoadenomatous, fibromatous, and leiomyomatous). This data may be recorded identifying every mm length as well as a gross classification of the near-end (inked-end), middle, and far-end of the biopsy sample. In addition, each biopsy sample may be scored as Good, Adequate, or Inadequate with respect to biopsy quality. Biopsy classification data may be collected and entered into a relational database to be later correlated with the spectra taken for each sample.

The advantage of having spectral data in the relational database is that it provides the capability to reduce and normalize these data in a variety of ways. In an exemplary data reduction and normalization scheme for newly acquired spectral data, the lowest amplitude observed in the entire population may be subtracted from each data point. Normalized amplitude values may be obtained by dividing the amplitudes by the mean amplitude calculated across each specific case. The final data set may be composed of mean amplitudes over a preset wavelength range, thus condensing the data points into a more manageable representation.

Initial screening of tissue biopsy classification based on biomorphometric data from whole-mount sections and three-dimensional computer models should be able to pick most outliers and line-sitters. Other techniques such as logistic regression and linear discriminant analysis may also be used. Further, non-linear approaches such as ANN, Gaussian processes, and support vector machine algorithms may be employed.

Determining the best choice of diagnostic test parameters is important. The prostatic tissue classification scheme must be able to predict a minimum of two possible outcomes (benign versus malignant) and more than two if Gleason sum classification of malignant tissue and PIN are to be included. A simplified classification scheme incorporating Gleason sum and PIN requires 16 possible outcomes whereas a comprehensive classification requires 26 possible outcomes. Determining 16 test parameters may be realized, for example, by dividing a 300-900 nm spectrum into 20 nm bands, which results in about 30 bands, each band providing one test parameter. Absorption features and slope variations that discriminate benign versus malignant tissue may also be used. Other possible parameters may include peak height ratios and factor analysis based on dividing the spectrum into domains. Factor or cluster analysis methods may also be helpful to identify promising groupings of the available data.

The diagnostic thresholds are sets of values of the diagnostic test parameters that determine the diagnostic outcome, i.e., no cancer, cancer or cancer grade, and the various benign conditions. A set of values for diagnostic thresholds may be determined based on their ability to properly predict the outcome, which may be assessed using standard medical measures. These measures include sensitivity, specificity, positive predictive value, negative predictive value, and test efficiency.

A preliminary ANN trained on spectral data from the UV-visible read fiber has been able to classify benign versus malignant tissue at 65-70% sensitivity. To eliminate outliers and improve the correlation of spectral data with pathological classification, pathological information from whole-mount sections was used to reconstruct three-dimensional computer models of RRP specimens. Pathological classification and tissue spectra were not the same due to several problems with this setup. First, some spectra may have been captured 5-10 mm away from the location where the biopsy was taken due to operator error. Second, the intensity of light sources and wide field of view of the probe may have excited surrounding tissue where spectral data for each biopsy could no longer be localized to the near end. An ANN trained on a reduced data set by eliminating the suspected outliers achieved a near perfect classification (sensitivity and specificity>90%) of normal versus malignant tissue (e.g., as shown in FIGS. 7A and 7B).

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. An optical biopsy needle device comprising:
an elongate biopsy needle having a distal end with a distal tip, said distal end having a tissue collecting cavity proximal to the distal tip and configured to biopsy tissue adjacent the cavity; and
a fiber optic bundle comprising at least one transmitter fiber having a first end extending from the distal tip and having a second end configured to connect to a spectral analysis device, said transmitter fiber configured for transmitting radiation from the spectral analysis device to the distal tip of the biopsy needle, and at least one receiver fiber having a first end extending to the distal tip and having a second end configured to connect to the spectral analysis device, said receiver fiber configured for transmitting radiation from the distal tip of the biopsy needle to the spectral analysis device, wherein the fiber optic bundle extends within the biopsy needle and wherein the first ends of both the transmitter fiber and the receiver fiber terminate at the distal end at the distal tip of the biopsy needle such that the transmitting fiber transmits radiation from the spectral analysis device to the tissue adjacent the distal tip and such that the receiver fiber transmits radiation from the tissue adjacent the distal tip to the spectral analysis device;
wherein at least one of:
the tissue collecting cavity is at the distal tip of the biopsy needle and the distal tip of the biopsy needle forms a flat surface; and
each of the first ends of the at least one transmitting fiber and at least one receiving fiber is flush with and exposed within the distal tip.

2. The optical biopsy needle device of claim 1, wherein the distal tip of the biopsy needle forms a flat surface and wherein the flat surface forms an angle with respect to an axial length of the biopsy needle.

3. The optical biopsy needle device of claim 1, wherein the distal end of the at least one transmitting fiber is separated by a distance from the distal end of the at least one receiving fiber wherein the distance is measured along the flat surface.

4. The optical biopsy needle device of claim 1, wherein the biopsy needle is housed within an outer sheath.

5. A method of obtaining a biopsy of tissue comprising
providing an optical biopsy needle device comprising an elongate biopsy needle having a distal end with a distal tip, said distal end configured to biopsy tissue spaced proximally from the distal tip, said device having a fiber optic bundle comprising at least one transmitter fiber for transmitting radiation to the distal tip and at least one receiver fiber for transmitting radiation from the distal tip, wherein the fiber optic bundle including the transmitter fiber and including the receiver fiber extends within the biopsy needle and wherein the fiber optic bundle including the transmitter fiber and including the receiver fiber each terminate at the distal tip of the biopsy needle such that the transmitter fiber transmits radiation to the tissue adjacent the distal tip and such that the receiver fiber transmits radiation from the tissue adjacent the distal tip;
connecting the fiber optic bundle of the optical biopsy needle device to a spectral analysis device;
positioning the distal tip of the biopsy needle adjacent to or within the tissue;
obtaining a spectral response associated with a distinct position of the tissue spaced proximally from the distal tip;
evaluating the spectral response with the spectral analysis device to determine whether the tissue is benign or malignant; and
actuating the biopsy needle device to obtain a portion of tissue spaced proximally from the distal tip at the distinct position and removing the portion of the tissue if the tissue is determined to be malignant.

6. The method of claim 5 further comprising delivering a therapeutic treatment to tissue at the distinct position determined to be malignant.

7. The method of claim 5, wherein the obtaining operation further comprises
illuminating the tissue with an incident broadband light source;
illuminating the tissue with at least one bandwidth-limited incident light source in the UV and near UC spectrum; and
collecting reflected and emitted light from the tissue.

8. The method of claim 5, wherein the obtaining operation further comprises
transmitting an excitation signal through the at least one transmitter fiber; and
receiving a fluorescence emission signal through the at least one receiver fiber.

9. The method of claim 8 wherein the evaluating operation determines whether the fluorescence emission signal is indicative of an abnormal level of an endogenous fluorophore in the tissue.

10. The method of claim 9, wherein the tissue is prostatic tissue and the evaluating operation determines whether the fluorescence emission signal is indicative of a level of tryptophan.

11. The method of claim 9, wherein the tissue is prostatic tissue and the evaluating operation determines whether the fluorescence emission signal is indicative of a level of NADH.

12. The method of claim 5, wherein the obtaining operation further comprises
transmitting an excitation signal through the at least one transmitter fiber; and
receiving an elastic scattering signal through the at least one receiver fiber.

13. The method of claim 5, wherein the evaluating operation further comprises analyzing the spectral response within an artificial neural network trained to differentiate between benign and malignant tissue to determine a morphology of each distinct position.

14. A system for determining morphology of tissue comprising:
a light source;
a spectrometer;
an elongate biopsy needle having a distal end with a distal tip, said distal end having a tissue collecting cavity proximal to the distal tip and configured to biopsy tissue adjacent the cavity;
a fiber optic bundle comprising at least one transmitter fiber having a first end extending from the distal tip and having a second end configured to connect to the spectrometer, said transmitter fiber configured for transmitting radiation from the spectrometer to the distal tip of the biopsy needle, and at least one receiver fiber having a first end extending to the distal tip and having a second end configured to connect to the spectrometer, said receiver fiber configured for transmitting radiation from the distal tip of the biopsy needle to the spectrometer, wherein the fiber optic bundle extends within the biopsy needle and wherein the first ends of both the transmitter fiber and the receiver fiber terminate at the distal end at the distal tip of the biopsy needle such that the transmitting fiber transmits radiation from the spectrometer to the tissue adjacent the distal tip and such that the receiver fiber transmits radiation from the tissue adjacent the distal tip to the spectrometer;
a detector coupled with the spectrometer that translates optical spectral data from the spectrometer into digital data;
a computer including a processor and memory that is coupled with and controls each of the light source, the spectrometer, and the detector;
a module stored in the memory and executed by the processor, wherein the module is trained to analyze the digital data corresponding to the optical spectral data to differentiate the tissue between benign and malignant.

15. The system of claim 14, wherein the light source further comprises an excitation unit comprising
an input port for receiving commands from the computer;
control circuitry for performing the commands received from the computer;
a broadband light source actuated by the control circuitry;
at least one bandwidth-limited incident light source in the UV and near UV spectrum; and
at least one lens aligned with each of the light sources for focusing light emitted from each of the light sources and transmitting the light to the at least one transmitting optical fiber.

16. The system of claim 14 further comprising a user interface wherein a user may direct operation of the computer.

17. The system of claim 14 further comprising a display for viewing results of the analysis.

18. The method of claim 5, wherein
the distal tip of the biopsy needle forms a flat surface; and
each of the distal ends of the at least one transmitting fiber and at least one receiving fiber is flush with and exposed within the flat surface.

19. The method of claim 18, wherein the flat surface forms an angle with respect to an axial length of the biopsy needle.

20. The method of claim 18, wherein the distal end of the at least one transmitting fiber is separated by a distance from the distal end of the at least one receiving fiber wherein the distance is measured along the flat surface.

21. The optical biopsy needle device of claim 5, wherein the biopsy needle is housed within an outer sheath.

22. The system of claim 14, wherein
the distal tip of the biopsy needle forms a flat surface; and
each of the first ends of the at least one transmitting fiber and at least one receiving fiber is flush with and exposed within the flat surface.

23. The system of claim 22, wherein the flat surface forms an angle with respect to an axial length of the biopsy needle.

24. The system of claim 22, wherein the distal end of the at least one transmitting fiber is separated by a distance from the distal end of the at least one receiving fiber wherein the distance is measured along the flat surface.

25. The system of claim 14, wherein the biopsy needle is housed within an outer sheath.

26. The optical biopsy needle device of claim 1 wherein the tissue collecting cavity is at the distal tip of the biopsy needle and the distal tip of the biopsy needle forms a flat surface.

27. The optical biopsy needle device of claim 26 wherein each of the first ends of the at least one transmitting fiber and at least one receiving fiber is flush with and exposed within the flat surface.

28. The optical biopsy needle device of claim 1 wherein each of the first ends of the at least one transmitting fiber and at least one receiving fiber is flush with and exposed within the distal tip.

* * * * *